United States Patent [19]

Klessing et al.

[11] Patent Number: 4,479,951
[45] Date of Patent: Oct. 30, 1984

[54] 1.4;3.6-DIANHYDROHEXITOL NITRATES SUBSTITUTED BY PURINE BASES, PROCESSES FOR THEIR PREPARATION AND PHARMACEUTICAL COMPOSITIONS

[75] Inventors: Klaus Klessing, Ettlingen; Shyam S. Chatterjee, Karlsruhe, both of Fed. Rep. of Germany

[73] Assignee: Dr. Willmar Schwabe GmbH & Co., Karlsruhe, Fed. Rep. of Germany

[21] Appl. No.: 285,406

[22] Filed: Jul. 20, 1981

[30] Foreign Application Priority Data

Jul. 25, 1980 [DE] Fed. Rep. of Germany ....... 3028273

[51] Int. Cl.³ .................. A61K 31/535; C07D 473/34
[52] U.S. Cl. .................. 424/248.57; 424/250; 544/118; 544/268; 544/277; 549/464
[58] Field of Search ...................... 544/268, 277, 118; 424/248.57, 250

[56] References Cited

U.S. PATENT DOCUMENTS 2,852,506  9/1958  Goldman et al. ................. 544/277
4,000,137 12/1976  Dvonch et al. .................. 544/277
4,087,603  5/1978  Hamill et al. .................... 544/277
4,321,376  3/1982  Otani et al. ..................... 544/277

Primary Examiner—Richard L. Raymond
Assistant Examiner—James H. Turnipseed
Attorney, Agent, or Firm—Toren, McGeady and Stanger

[57] ABSTRACT 1.4;3.6-Dianhydrohexitol nitrates substituted by purine bases, namely, adenyl-desoxy-1.4;3.6-dianhydrohexitol nitrates of the general formula Ia as well as theophyllinyl-desoxy-1.4;3.6-dianhydrohexitol nitrates of the general formula Ib,

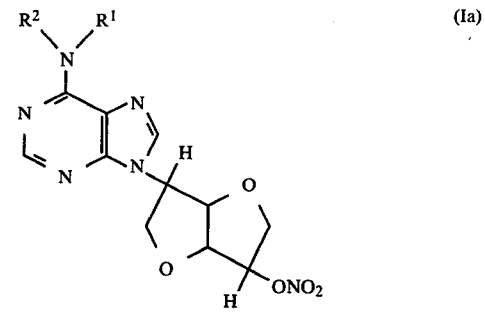

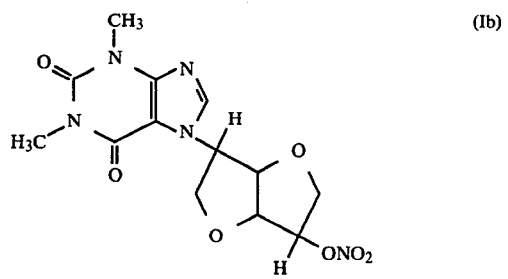

wherein $R^1$ and $R^2$ are the same or different and, independently of one another signify (a) a hydrogen atom,
(b) a straight-chained or branched alkyl group with 1 to 7 C-atoms,
(c) an ω-phenylalkyl group, whereby the alkyl group has 1 to 7 C-atoms and whereby the phenyl ring can be halogen-substituted in the p-position, or wherein
(d) $R^1$ signifies one of the residues given under (a) to (c) and $R^2$ an acyl radical or an aliphatic, possibly methyl-substituted monocarboxylic acid with 2 to 7 C-atoms, or wherein
(e) $R^1$ and $R^2$, together with the nitrogen atom to which they are bound, represent the residue of a cyclic, non-aromatic, secondary amine possibly containing a further hetero atom, as well as their physiologically acceptable acid-addition salts.

Process for the preparation of said compounds and pharmaceutical compositions containing said compounds.

22 Claims, No Drawings

1.4;3.6-DIANHYDROHEXITOL NITRATES SUBSTITUTED BY PURINE BASES, PROCESSES FOR THEIR PREPARATION AND PHARMACEUTICAL COMPOSITIONS

BACKGROUND OF THE INVENTION

1. Field of the Invention

The invention concerns 1.4;3.6-dianhydrohexitol nitrates substituted by purine bases, namely, adenyl-desoxy-1.4;3.6-dianhydrohexitol nitrates of the general formula Ia,

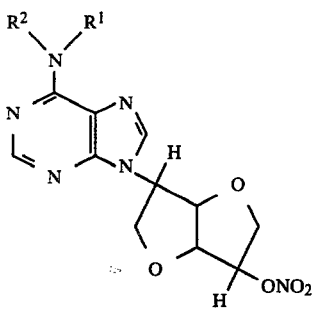

as well as theophyllinyldesoxy-1.4;3.6-dianhydrohexitol nitrates of the general formula Ib:

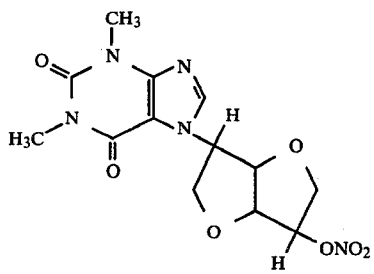

2. Description of the Prior Art

The basic structure of these compounds consists of one of the stereoisomeric 1.4;3.6-dianhydrohexitols convertible into one another by epimerisation, namely, either 1.4;3.6-dianhydro-L-iditol (="isoidide") (II),

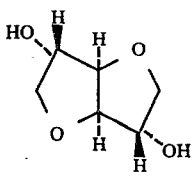

in which the OH groups in the 2- and 5-position each have the exo-configuration, or 1.4;3.6-dianhydro-D-glucitol (="isosorbide") (III)

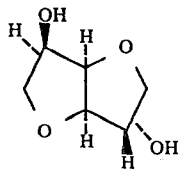

which has an exo-standing and an endo-standing OH group and thus—in the case of various substituents in the 2- and 5-position—occurs in two isomeric forms.

Finally, the basic structure of some intermediate products consists of 1.4;3.6-dianhydro-D-mannitol (="isomannide") (IV),

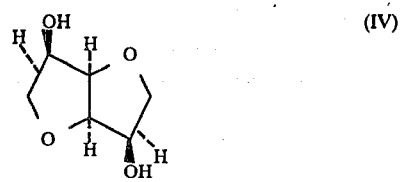

which has two endo-standing OH groups.

Since, in contradistinction to the glucitol derivatives, in the case of the iditol and mannitol derivatives a difference between the 2- and 5-substituents is not possible because the $C^2$ atom, in the case of rotation of the molecule through 180°, becomes the $C^5$ atom, references to the 5-position or 2-position of substituents is, in the case of these derivatives, superfluous. However, for a better comparison of the structures of the individual compounds with the general formulae, the isoidide derivatives are here all referred to as 5-purinylisoidide derivatives since they result from isosorbide derivatives acyl substituted in the 5-position. Correspondingly, the isomannide acyl derivatives used as starting compounds are referred to as 2-acylisomannide derivatives since the 2-purinylisosorbide derivatives are prepared from them.

A brief summary of the stereoisomerism of the 1.4;3.6-dianhydrohexitols is given by J. A. Mills in Advances in Carbohydrate Chem., 10, 1–53 (1955).

Furthermore, the invention is concerned with processes for the preparation of the initially mentioned 1.4;3.6-dianhydrohexitol mononitrates substituted by purine bases, as well as pharmaceutical compositions which contain the compounds according to the invention.

The nitrates of 1.4;3.6-dianhydro-D-glucitol (also called 1.4;3.6-dianhydro-D-sorbitol) are known e.g. from U.S. Pat. No. 3,886,186, namely, not only in the 2- and 5-mononitrates but also the 2,5-dinitrates of isosorbide. These nitrates, especially the dinitrate, which is already commercially available as a medicament, are pharmacologically-active substances with haemodynamic, vasodilatory and antiaginous effectiveness, which are used especially in the case of coronary insufficiency and for the treatment of angina pectoris.

The pharmacokinetics of the dinitrate and of the mononitrates of isosorbide, isomannide and isoidide have been described by Bogaert and Rosseel in Naunyn-Schmiedeberg's Arch. Pharmacol., 275, 339 (1972).

However, it has been shown that the nitrates cause unpleasant side effects, especially headaches. Furthermore, the mononitrates are more poorly resorbed than, for example, isosorbide dinitrate (ISDN). It is also to be added that the dinitrates of isosorbide, isomannide and isoidide can only be prepared and handled with special precautionary measures, since they are explosive.

Thus, there is a need for the making available of new pharmaceutical agents with the same activity spectrum but which do not display the mentioned disadvantages and for the provision of new 1.4;3.6-dianhydrohexitol mononitrates which can be used as active components of such pharmaceutical agents.

The task forming the basis of the invention consists in satisfying the mentioned need, the solution of this problem in the making available of the substances according to the invention.

SUMMARY OF THE INVENTION

Consequently, the subject of the invention are:
1. 5-(9-adenyl)-5-desoxy-1.4;3.6-dianhydro-L-iditol 2-nitrates (=2-(9-adenyl)-2-desoxy-1.4;3.6-dianhydro-L-iditol 5-nitrates) of the general formula Ic,

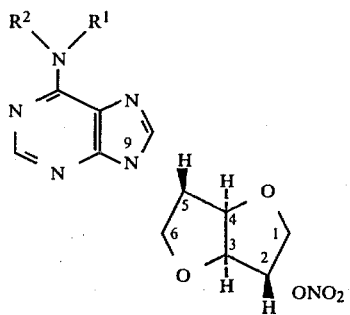

wherein $R^1$ and $R^2$ are the same or different and, independently of one another represent
 (a) a hydrogen atom,
 (b) a straight-chained or branched alkyl group with 1-7 C-atoms,
 (c) an ω-phenylalkyl group, whereby the alkyl group has 1 to 7 C-atoms and whereby the phenyl ring can be halogen-substituted in the p-position, or wherein
 (d) $R^1$ signifies one of the residues given under (a) to (c) and $R^2$ an acyl residue of an aliphatic, possibly methyl-substituted monocarboxylic acid with 2 to 7 C-atoms, or wherein
 (e) $R^1$ and $R^2$, together with the nitrogen atom to which they are bound, represent the residue of a cyclic, non-aromatic secondary amine possibly containing a further hetero atom,
as well as their physiologically acceptable acid-addition salts.

2. 2-(9-Adenyl)-2-desoxy-1.4;3.6-dianhydro-D-glucitol 5-nitrates of the general formula Id,

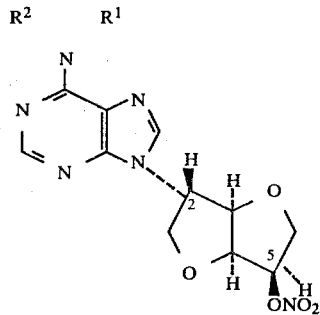

wherein $R^1$ and $R^2$ possess the meanings given under (1.), as well as their physiologically acceptable acid-addition salts.

3. 5-(9-Adenyl)-5-desoxy-1.4;3.6-dianhydro-D-glucitol 2-nitrates of the general formula Ie,

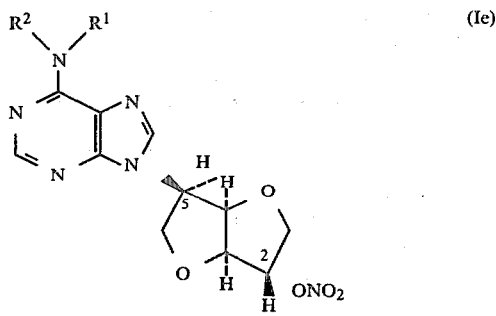

wherein $R^1$ and $R^2$ possess the meanings given under (1.), as well as their physiologically acceptable acid-addition salts.

4. 5-(7-Theophyllinyl)-5-desoxy-1.4;3.6-dianhydro-L-iditol 2-nitrate (=2-(7-theophyllinyl)-2-desoxy-1.4;3.6-dianhydro-L-iditol 5-nitrate), as well as its physiologically acceptable acid-addition salts.

5. 2-(7-Theophyllinyl)-2-desoxy-1.4;3.6-dianhydro-D-glucitol 5-nitrate, as well as its physiologically acceptable acid-addition salts.

The compounds according to the invention possess coronary flowthrough-increasing, spasmolytic and blood pressure-lowering effectiveness. They are suitable for the treatment of coronary diseases, for the treatment and prophylaxis of attacks of angina pectoris, for the after-treatment of heart infarcts and for the treatment of cardiac insufficiencies. The new compounds possess a good therapeutic range. The oral absorption is especially good and the period of action long. Furthermore, they bring about an improvement of the peripheral blood flow and of brain blood flow.

The handling and preparation of the compounds according to the invention is less dangerous than, for example, in the case of the known ISDN because they are not explosive.

DESCRIPTION OF THE PREFERRED EMBODIMENT

In the 1.4;3.6-dianhydrohexitol basic structure, the compounds according to the invention possess 4 asymmetrical C-atoms and are present in optically-active form since, as starting product, optically pure 1.4;3.6-dianhydrohexitols are used which are easily obtainable from naturally-occurring sugar alcohols.

The compounds according to the invention can be prepared starting from the epimeric, unsubstituted 1.4;3.6-dianhydrohexitols, thus starting from L-isoidide, D-isosorbide and D-isomannide, whereby, in the case of D-isosorbide as starting compound, two different synthesis routes are possible.

According to the invention, the first route consists in that the corresponding 1.4;3.6-dianhydrohexitol is converted with a sulphonic acid chloride, preferably with methanesulphonic acid chloride or toluenesulphonic acid chloride, in a suitable anhydrous solvent and in the presence of an adjuvant base, preferably in pyridine or in chloroform/triethylamine, at reduced temperature, preferably between −20° and +10° C., into the corresponding mono-O-acyl-1.4;3.6-dianhydrohexitol and the acyl derivative is reacted with the alkali metal salt, usually the sodium or potassium salt, of the desired purine derivative, preferably of adenine, 6-N-substituted-adenine, theophyllin, 6-methyl-mercaptopurine or 6-chloropurine, in a dipolar aprotic solvent, e.g. dimethylformamide, dimethyl sulphoxide, tetramethylurea, diethers of ethyleneglycol, preferably in dimethylformamide or dimethyl sulphoxide, at an elevated temperature, preferably at 80° to 130° C., under an inert gas atmosphere ($N_2$ or Ar).

The exchange of the mesylate or tosylate group by the adenyl, 6-N-substituted adenyl, theophyllinyl, 6-chloropurinyl or 6-methylmercaptopurinyl radical taking place in this first step takes place in the manner of reaction of a typical bimolecular nucleophilic substitution ($S_N2$ reaction), which always involves a reversal of the configuration on the central carbon atom. This reversal of configuration, which is also known to the expert under the terms "inversion" or "Walden inversion", is the reason why, from the 1.4;3.6-dianhydro-D-glucitol 5-acyl derivative, in which the acyl radical is present in the 5-endo-position, there always results the 1.4;3.6-dianhydro-L-iditol derivative substituted in the 5-position by the adenyl, 6-N-substituted-adenyl, theophyllinyl, 6-chloropurinyl or 6-methylmercaptopurinyl radical, in which the substituent entering into the molecule in place of the acyl radical no longer stands in the endo-position but rather in the exo-position. The Walden inversion involved with the $S_N2$ reaction is, in entirely the corresponding manner, responsible for the fact that from the corresponding iditol acylate there always results the glucitol derivative endo-substituted in the 5-position and from the mannitol acylate the corresponding glucitol derivative exo-substituted in the 2-position.

Thus, completely analogously, from the 1.4;3.6-dianhydro-D-glucitol-2-acylate, in which the acyl radical is present in the exo-position, there should result the corresponding 2-purinyl-1.4;3.6-dianhydro-D-mannitol derivative in which the purine radical should then be endo-standing. However, it has been shown that this reaction, thus the substitution of the 2-exo-acyl radical by the voluminous purine radical, as a result of steric hindrance, does not take place under the conditions employed according to the invention.

The compounds resulting in the hitherto described first step of the first synthesis route have, in the 6-position of the purine ring system in the case of adenine, an unsubstituted amino group, in the case of methylmercaptopurine the $CH_3S$-group and in the case of chloropurine the chlorine residue. The 6-N-substituted adenyl derivatives are, starting from the 6-methylmercapto- or 6-chloropurine derivatives, which thus represent valuable intermediate products for the preparation of the compounds according to the invention, prepared in that one reacts the methylmercapto- or chloropurine derivative with the desired primary or secondary alkylamine with a straight-chained or branched alkyl group with 1 to 7 C-atoms or an ω-phenylalkylamine with an alkyl group of 1 to 7 C-atoms or a corresponding ω-phenylalkylamine in which the phenyl ring is halogen-substituted in the p-position, thus, for example with p-chlorobenzylamine, p-chlorophenylethylamine, p-chlorophenylpropylamine. The purine derivatives substituted in the 6-position with a heterocyclic secondary amine are obtained from the corresponding methylmercapto- or chloropurine derivatives by reaction with the corresponding cyclic, nonaromatic secondary amines possibly containing a further hetero atom, for example with pyrrolidine, piperidine, piperazine, morpholine or any of their substituted derivatives. In an analogous manner, the unsubstituted adenyl derivative can be obtained by reaction of the 6-chloro- or 6-methylmercaptopurinyl derivative with ammonia.

The reaction of the methylmercapto- or chloropurine derivatives with ammonia, the desired primary or secondary alkylamine, possibly p-chloro-substituted ω-phenylalkylamine or cyclic non-aromatic secondary amine possibly containing a further hetero atom takes place at an elevated temperature and increased pressure, preferably at a temperature of 100°–170° C. and a pressure of 2–50 ats., especially advantageously at a pressure of 2–20 ats., under an inert gas atmosphere ($N_2$ or Ar), whereby ammonia or the corresponding amine are used in excess, preferably in 2–10 fold molar excess, possibly in the presence of a solvent, e.g. methanol, ethanol, butanol.

Instead of the subsequent substitution of the 6-chloro- or 6-methylmercapto group of the purine-1.4;3.6-dianhydrohexitol derivative, the hexitol acylates can, in the first step, also be reacted immediately, in an analogous manner, with the alkali metal salts of the adenine derivative already correspondingly substituted on the 6-N-atom. Correspondingly substituted adenines, insofar as they are not known from the literature, can be obtained from 6-chloro- or 6-methylmercaptopurine by heating with the corresponding amines.

The 5-(7-theophyllinyl)-, 5-(9-adenyl)- and 5-(6-N-substituted-9-adenyl)-isohexide derivatives resulting in the course of the hitherto described first synthesis route each have a free hydroxyl group in the 2- or 5-position of the 1.4;3.6-dianhydrohexitol ring system. This free hydroxyl group is esterified in per se known manner with nitric acid, with nitrating acid or with a mixture of nitric acid and glacial acetic acid/acetic anhydride to give the corresponding mononitrates of the general formulae Ia to Ie.

Subsequently, in the case of the 9-adenyl- or 6-N-Monosubstituted-9-adenylisohexide nitrates, by the reaction thereof with an acid chloride or anhydride of an aliphatic, possibly methyl-substituted monocarboxylic acid with 2 to 7 C-atoms, for example with pivaloyl chloride, acetic acid chloride, acetic anhydride or the like, one can prepare the corresponding acyl derivatives in the manner of a Schotten-Baumann reaction or of the Einhorn variant thereof.

The hitherto described first route according to the invention for the preparation of the compounds according to the invention, in which the corresponding isohexide is converted with a sulphonic acid chloride, preferably with methanesulphonic acid chloride or toluenesulphonic acid chloride, into the corresponding monoacyl-1.4;3.6-dianhydrohexitol, has the disadvantage that, in the case of the acylation, there results not only the corresponding 5-O-acyl derivative or 2-O-acyl derivative but simultaneously also the 2,5-diacyl derivative so that, in the case of the isoidide and isomannide derivatives, in each case the monoacyl compound must be separated from the diacylate, whereas in the case of the isosorbide, in which two stereoisomeric monoacyl derivatives result, besides the diacylate, the desired acylate must be isolated from the mixture of the three acyl derivatives. The separation of the acylate mixture takes place either by fractional crystallisation, fraction extraction or with the help of other per se known methods.

The laborious and time-consuming separation of the acylate mixture disappears, however, in the case of the use of the second synthesis route according to the invention to the 5-purinylisoidide derivatives in that 1.4;3.6-dianhydro-D-glucitol is reacted quantitatively with an excess of sulphonic acid chloride, preferably methanesulphonyl chloride or toluenesulphonyl chloride, in pyridine or chloroform/triethylamine, to give the corresponding 1.4;3.6-dianhydro-D-glucitol 2,5-diacylate.

The diacylate is then reacted with the alkali metal salt of adenine, 6-N-substituted adenine or theophyllin, under conditions corresponding to those described in the first synthesis route, whereby—because of the above-described steric hindrance of the substitution in the 2-exo-position—only the 5-endo-acylate radical is substituted by the corresponding purine residue in the case of simultaneous inversion of the configuration on the $C^5$-atom. Thus, there results the 5-(9-adenyl)-, or 5-(6-N-substituted 9-adenyl)-, or 5-(7-theophyllinyl)-5-desoxy-1.4;3.6-dianhydro-L-iditol 2-acylate, which is saponified by hydrolysis to the corresponding adenyl, substituted adenyl or theophyllinyl-isoidide derivative and subsequently—in the same way as in the case of the first synthesis route—is esterified in per se known manner with nitric acid, nitrating acid or with a mixture of nitric acid and glacial acetic acid/acetic anhydride and is possibly subsequently acylated on the 6-N-atom analogously to the first synthesis route.

The degree of steric hindrance in the case of the nucleophilic substitution of the 2-exo-acylate group in the isosorbide diacylate is temperature-dependent. In order to obtain the purinyl-isoidide monoacylate as quantitatively as possible from the corresponding diacylate, one works, therefore, according to the invention, preferably at a temperature of 80°–100° C. since, at temperatures above 100° C., the 2-exo-acyl group, even if only to a small extent, is attacked by the purine derivative employed. As solvents, there are hereby preferably employed dimethylsulphoxide or dimethylformamide.

In order to convert the compounds according to the invention into their physiologically acceptable salts, there can be used inorganic acids and mineral acids, such as hydrohalic acids and phosphoric acids, as well as organic acids, such as carboxylic and sulphonic acids, for example malonic, succinic, lactic, tartaric, malic, benzoic, salicylic, citric, ascorbic, nicotinic or p-toluenesulphonic acid. The free bases can again be liberated from the acid-addition salts by treatment with strong bases, for example sodium or potassium hydroxide.

Furthermore, the subject of the invention are pharmaceutical compositions which, besides the usual carrier and addition materials, contain at least one of the compounds according to the invention or of their physiologically acceptable salts. These compositions can be used as medicaments in human and veterinary medicine. Conventional carrier materials are, for example, water, vegetable oils, polyethylene glycols, glycerol esters, gelatine, carbohydrates, such as lactose or starch, magnesium stearate, talc, Vaseline. Conventional additive materials are, for example, preserving, stabilising, lubricating, wetting agents, emulsifiers, physiologicaly acceptable salts, buffer substances, colouring, flavouring and aroma materials. The selection of the carrier and additive materials depends upon whether the compounds according to the invention are to be administered enterally, parenterally or topically.

The compounds according to the invention can also be administered in admixture with other active materials, for example vitamins or known, commercially-available heart-circulation agents, particularly also with β-receptor blockers.

Example of a pharmaceutical composition:

For the preparation of tablets each of 100 mg. individual weight, each of which contains 5 mg. of active material, one needs I. 5 g. 5-(9-adenyl)-5-desoxy-1.4;3.6-dianhydro-L-iditol 2-nitrate hydrochloride semihydrate
II. 54 g. microcrystalline cellulose
III. 20 g. lactose
IV. 20 g. maize starch
V. 0.5 g. colloidal silicic acid
IV. 0.6 g. magnesium stearate The substances I–IV are dry mixed for 10 minutes, subsequently the mixture is added to the substances V and VI, one mixes for a further 10 minutes and presses the so obtained powder on a tabletting machine to give tablets of 100 mg. individual weight.

Each of the compounds and intermediate products according to the invention mentioned in the following Examples represents an especially suitable agent for the preparation of pharmaceutical compositions.

The abbreviations contained in the Examples have the following meanings:

| | |
|---|---|
| m.p. | = melting point (uncorrected) |
| (decomp.) | = decomposition |
| d | = density |
| $[\alpha]_D^{25}$ | = optical rotation at 25° C., sodium D line. |

After the optical rotational values are given the concentrations of the measured solutions, whereby c 2 means, for example, a concentration of 2 g./100 ml. of solution; the solvent is, in each case, given separately. All temperatures are given in °C.

EXAMPLE NO. 1

5-(9-Adenyl)-5-desoxy-1.4;3.6-dianhydro-L-iditol 2-nitrate:

(a) 1.4;3.6-Dianhydro-D-glucitol 2-methanesulphonate, 5-methanesulphonate and 2,5-dimethanesulphonate:

To a solution of 4.82 kg. (33 mol) 1.4;3.6-dianhydro-D-glucitol in 24 liters of pyridine one adds dropwise, with the exclusion of moisture, stirring and cooling to −15°, within the course of several hours, 3.1 liters (40 mol) methanesulphonic acid chloride. Subsequently, one further stirs for 15 hours without cooling. One distils off the pyridine in vacuo, adds 15 liters of water to the oily residue, boils up and allows to cool. Suction filtration, washing with 4 liters of water and drying of the crystalline precipitate gives 2.22 kg. (7.34 mol) 1.4;3.6-dianhydro-D-glucitol 2,5-dimethanesulphonate. The filtrate is neutralised, with stirring and water cooling, with about 1.5 kg. sodium hydroxide and evaporated to dryness at about 70° in a vacuum. The dry residue is continuously hot extracted with, in all, 30 liters of chloroform and the extract filtered hot. One allows the extract to stand for 15 hours at 20°, filters off the crystalline precipitate with suction, washes it twice with 2 liter amounts of chloroform, dries and obtains 2.3 kg. (10.26 mol) 1.4;3.6-dianhydro-D-glucitol 5-methanesulphonate. The combined filtrates are evaporated in a vacuum and the residue dissolved hot in 22 liters of ethanol. One leaves to stand for 15 hours at 20°, filters off the crystalline precipitate with suction, washes it twice with 3 liter amounts of ethanol, dries and obtains 0.65 kg. (2.90 mol) 1.4;3.6-dianhydro-D-glucitol 2-methanesulphonate. Evaporation of the filtrate gives 2.21 kg. (9.85 mol) of a mixture of the two isomeric monomethanesulphonates which, according to need, can be further separated by repetition of the alternating crystallisations from chloroform and ethanol or, by esterification with methanesulphonic acid chloride in pyridine, is completely converted into 1.4;3.6-dianhydro-D-glucitol 2,5-dimethanesulphonate. Analytical amounts of the methanesulphonates give, after recrystallisation, correct elementary analyses and the melting points and optical rotations set out in Table 1:

TABLE 1

| 1.4; 3.6-dianhydro-D-glucitol- | recrystallised from | m.p. [°C.] | $[\alpha]_D^{25}$ |
|---|---|---|---|
| 2-methanesulphonate | chloroform | 135–138.5 | 62.5 (c 2; acetone) |
| 5-methanesulphonate | chloroform | 123–124 | 75.9 (c 2; methanol) |
| 2.5-dimethanesulphonate | ethanol/acetone | 127–128 | 74 (c 2; acetone) |

(b) 5-(9-Adenyl)-5-desoxy-1.4;3.6-dianhydro-L-iditol:

Under an atmosphere of nitrogen and with stirring, one adds a solution of 22.4 g. (0.1 mol) 1.4;3.6-anhydro-D-glucitol 5-methane sulphonate in 100 ml. anhydrous dimethyl sulphoxide dropwise at 100° to a suspension of 15.7 g. (0.1 mol) adenine sodium salt in 200 ml. anhydrous dimethyl sulphoxide and then stirs for 8 days at 100°. One distils off the solvent in vacuo and successively extracts the residue at boiling temperature with 100 ml. chloroform and n-butanol. The chloroform extract is concentrated to about 300 ml., by the addition of 600 ml. petroleum ether, the crude product is precipitated out and separated off; the filtrate is discarded. The butanol extract gives, after evaporation in vacuo further crude product. The combined crude products are recrystallized from 400 ml. ethanol. One obtains 9.2 g. (35 mmol) 5-(9-adenyl)-5-desoxy-1.4;3.6-dianhydro-L-iditol. The evaporated mother liquor is dissolved in 200 ml. water and continuously extracted with about 1 liter of a mixture of chloroform/butanol 9/1. Evaporation of the extract and recrystallisation from chloroform gives a further 3.9 g. (15 mmol) of pure product.

M.p. 202.5°–204.5° $[\alpha]_D^{25}$ 22.2 (c 1; water). elementary analysis: $C_{11}H_{13}N_5O_3$ (263.25). calc.: C (50.19), H (4.98), N (26.60); found: C (50.39), H (5.04), N (26.69).

(c) 5-(9-Adenyl)-5-desoxy-1.4;3.6-dianhydro-L-iditol 2-nitrate:

With stirring and cooling to −15°, one slowly mixes 35 ml. of 95% nitric acid (d=1.5) with 2.5 g. urea and then adds portionwise thereto a total of 4.0 g. (15 mmol) 5-(9-adenyl)-5-desoxy-1.4;3.6-dianhydro-L-iditol. One further stirs for 1 hour at −15° and slowly pours the mixture, with cooling and stirring, into 300 ml. of cold water. Subsequently, it is neutralised by the addition of 85 g. potassium hydrogen carbonate and extracted five times with 200 ml. amounts of a mixture of chloroform/methanol 95/5. After drying over anhydrous sodium sulphate, the combined extracts are evaporated at about 50° in vacuo and recrystallized from chloroform/petroleum ether. One obtains 3.8 g. (12.3 mmol) 5-(9-adenyl)-5-desoxy-1.4;3.6-dianhydro-L-iditol 2-nitrate of m.p. 158°–160° (decomp.). For analysis, one again recrystallises from chloroform/petroleum ether.

m.p. 162°–3° (decomp.) $[\alpha]_D^{25}$ 80.9 (c 2; chloroform). elementary analysis: $C_{11}H_{12}N_6O_5$ (308.26). calc.: C (42.86), H (3.93), N (27.26); found: C (42.38), H (3.93), N (27.38).

EXAMPLE NO. 2

5-(9-Adenyl)-5-desoxy-1.4;3.6-dianhydro-L-iditol 2-nitrate:

(a) 5-(9-Adenyl)-5-desoxy-1.4;3.6-dianhydro-L-iditol 2-methanesulphonate:

A mixture of 20.15 g. (150 mmol) adenine sodium salt, 30.2 g. (100 mmol) 1.4;3.6-dianhydro-D-glucitol 2,5-dimethanesulphonate and 300 ml. dimethyl sulphoxide is heated for 24 hours, with stirring, to 100°. After cooling, one mixes with 600 ml. water, filters off with suction the precipitate consisting of reaction product and unreacted dimethanesulphonate and then washes twice with 50 ml. amounts of water. The precipitate is stirred with 600 ml. chloroform, whereby the dimethanesulphonate goes into solution and pure product remains behind. One obtains further product by two extractions of the chloroform phase with 100 ml. amounts of 2 molar hydrochloric acid neutralisation of the hydrochloric acid phase with dil. aqueous sodium hydroxide solution. Subsequenty, one recrystallises from ethanol and obtains 17.5 g. (51.3 mmol) 5-(9-adenyl)-5-desoxy-1.4;3.6-dianhydro-L-iditol 2-methanesulphonate of m.p. 238°–240°.

$[\alpha]_D^{25}$ 39.8 (c 1; dimethylformamide). Elementary analysis: $C_{12}H_{15}N_5O_5S$ (341.34). calc.: C (42.22), H (4.43), N (20.52), S (9.39); found: C (42.36), H (4.34), N (20.76), S (9.2).

(b) 5-(9-Adenyl)-5-desoxy-1.4;3.6-dianhydro-L-iditol:

A solution of 30.6 g. (765 mmol) sodium hydroxide in 250 ml. water is added, with stirring, at a rate of 10 ml./hour to a mixture, boiling under reflux, of 87 g. (225 mmol) 5-(9adenyl)-5-desoxy-1.4;3.6-dianhydro-L-iditol 2-methanesulphonate and 4 liters of water and subsequently stirs under reflux for 5 hours. After cooling, one neutralises the solution with 510 mmol hydrochloric acid, evaporates in vacuo, dries the residue azeotropically with n-butanol and boils it three times with 2 liter amounts of n-butanol. The butanol extracts are evaporated in vacuo and recrystallised from ethanol. One obtains 41.5 g. (158 mmol) 5-(9-adenyl)-5-desoxy-1.4;3.6-dianhydro-L-iditol of m.p. 203°. One obtains a further 10 g. (38 mmol) of product by evaporation of the mother liquor, extraction of the residue with chloroform and evaporation of the chloroform extract.

(c) 5-(9-Adenyl)-5-desoxy-1.4;3.6-dianhydro-L-iditol 2-nitrate:

With stirring and cooling to −20°, one adds portionwise a total of 15 g. urea to 200 ml. of 95% nitric acid (d=1.5). At −20°, one adds thereto, within 1 hour, 41 g. (156 mmol) 5-(9-adenyl)-5-desoxy-1.4;3.6-dianhydro-L-iditol in small portions and then stirs for 1 hour at about −15°. The clear reaction mixture is slowly poured, with stirring, into 600 ml. of ice water, whereby the main amount of the reaction product crystallises out in the form of the hydrogen nitrate. The crystallisate is filtered off with suction, washed twice with 100 ml. amounts of water, suspended in 500 ml. water, converted into the base by the addition of 2 molar aqueous sodium hydroxide solution, again filtered off with suction and washed neutral with water. One obtains further product by neutralisation of the filtrate of the ice water precipitation with aqueous sodium hydroxide solution (4.4 mol), combines with all the previously obtained filtrates and wash waters, extracts twice with 1 liter amounts of chloroform and evaporates the chloroform extracts in vacuo. The combined crude bases are dissolved in 500 ml. ethanol and, by the addition of 12 ml. of 37% hydrochloric acid (144 mmol), converted into the hydrochloride, which crystallises out. One filters off with suction, washes with 100 ml. ethanol, concentrates the filtrate to 150 ml. and again filters off with suction and then washes with a little ethanol. One obtains 43.3 g. (126 mmol) 5-(9-adenyl)-5-desoxy-1.4;3.6-dianhydro-L-iditol 2-nitrate as hydrochloride, with ½ mole of water of crystallisation.

M.p. 204°-205° decomp. $[\alpha]^{25}_D$ 28.6 (c 0.5; water). Elementary analysis: $C_{11}H_{12}N_6O_5 \times HCl \times \frac{1}{2}H_2O$ (353.72). calc.: C (37.35), H (3.99), N (23.76), Cl (10.02); found: C (37.35), H (3.95), N (23.73), Cl (10.1).

The hydrogen nitrate has, after recrystallisation from methanol, the m.p. 188°-190° and $[\alpha]^{25}_D$ 26.8 (c 0.5; water).

Elementary analysis: $C_{11}H_{12}N_6O_5 \times HNO_3$ (371.27). calc.: C (35.59), H (3.53), N (26.41); found: C (35.71), H (3.46), N (26.30).

EXAMPLE NO. 3

5-(6-Methylaminopurin-9-yl)-5-desoxy-1.4;3.6-dianhydro-L-iditol 2-nitrate:

(a) 5-(6-Methylmercaptopurin-9-yl)-5-desoxy-1.4;3.6-dianhydro-L-iditol:

A solution of 166 g. (1 mol) 6-methylmercaptopurine and 40 g. (1 mol) sodium hydroxide in 1 liter of methanol is evaporated in vacuo and dried at 140° to constant weight. One obtains 188 g. (1 mol) of the 6-methylmercaptopurine 9-sodium salt. This is suspended, together with 224 g. (1 mol) 1.4;3.6-dianhydro-D-glucitol 5-methanesulphonate, in 3 liters dimethylformamide and heated to 130° for 24 hours, with stirring and under an atmosphere of nitrogen. Subsequently, one distils off the dimethylformamide in vacuo, takes up the residue in 2 liters of water and continuously extracts in a rotary perforator with about 5 liters chloroform. The chloroform extract is clarified over anhydrous sodium sulphate, filtered and evaporated. The remaining oily reaction product solidifies upon triturating with some water to give a crystalline slurry which is stirred with 600 ml. water, filtered off with suction and washed 2 times with 75 ml. water. Subsequently, one dries in a vacuum drying cabinet at 120° to constant weight and obtains 147 g. (0.5 mol) 5-(6-methylmercaptopurin-9-yl)-5-desoxy-1.4;3.6-dianhydro-L-iditol. For analysis, one recrystallises from chloroform/toluene. M.p. 146°-8° $[\alpha]^{25}_D$ 22.5 (c 1; chloroform).

elementary analysis: $C_{12}H_{14}N_4O_3S$ (294.33). calc.: C (48.97), H (4.79), N (19.04), S (10.89); found: C (48.66), H (4.70), N (18.70), S (10.6).

(b) 5-(6-Methylaminopurin-9-yl)-5-desoxy-1.4;3.6-dianhydro-L-iditol:

A mixture of 8.8 g. (30 mmol) 5-(6-methylmercaptopurin-9yl)-5-desoxy-1.4;3.6-dianhydro-L-iditol, 8.5 ml. of 33% methanolic methylamine solution (90 mmol) and 100 ml. water is stirred at 130° for 20 hours in a closed autoclave. After cooling and decompressing, one evaporates to dryness, dissolves the residue in 50 ml. water and continuously extracts with choroform. Evaporation of the chloroform extract, dried over anhydrous sodium sulphate, gives 7.1 g. (25.6 mmol) of oily crude product which, for purification, is converted into the hydrochloride and recrystallised from methanol.

M.p. 247°-250° (decomp.) $[\alpha]^{25}_D$ 35.9 (c 1; water). elementary analysis: $C_{12}H_{15}N_5O_3 \times HCl$ (313.74). calc.: C (45.94), H (5.14), N (22.32), Cl (11.30); found: C (46.08), H (5.25), N (22.29), Cl (11.3 ).

(c) 5-(6-Methylaminopurin-9-yl)-5-desoxy-1.4;3.6-dianhydro-L-iditol 2-nitrate:

To a mixture of 20 ml. glacial acetic acid, 2.5 g. (9 mmol) 5-(6-methylaminopurin-9-yl)-5-desoxy-1.4;3.6-dianhydro-L-iditol and 0.6 g. (10 mmol) urea one adds dropwise, with stirring and cooling to 10°-15°, a solution of 1.7 ml. (40 mmol) 95% nitric acid (d=1.5) in 10 ml. glacial acetic acid and subsequently 10 ml. acetic anhydride. One stirs for 3 hours at 10°-15°, dilutes with water to a total volume of 200 ml., stirs, with the addition of 5 g. sodium hydrogen carbonate, for about 30 mil., filters off with suction the reaction product obtained as a finely particulate precipitate, washes with 20 ml. water and dries. One obtains 1.4 g. (3.6 mmol) 5-(6-methylaminopurin-9-yl)-5-desoxy-1.4;3.6-dianhydro-L-iditol 2-nitrate in the form of the hydrogen nitrate. A further 0.7 g. (1.8 mmol) of product is obtained by extraction of the filtrate with 3×100 ml. chloroform, washing of the chloroform extract with 50 ml. water, evaporation in a vacuum and reprecipitation of the residue from ether/petroleum ether. The analytical sample is recrystallized from water/isopropanol. M.p. 193°-197° (decomp.) $[\alpha]^{25}_D$ 28.6 (c 1; water). Elementary analysis: $C_{12}H_{14}N_6O_5 \times HNO_3$ (385.30). calc.: C (37.40), H (3.92), N (25.45); found: C (37.34), H (3.94), N (25.21).

A part of the product is converted into the hydrochloride and recrystallised from ethanol/isopropanol.

M.p. 201°-204° (decomp.) $[\alpha]^{25}_D$ 29.1 (c 1; water). Elementary analysis: $C_{12}H_{14}N_6O_5 \times HCl$ (358.74). calc.: C (40.18), H (4.21), N (23.43), Cl (9.88); found: C (40.35), H (4.24), N (23.49), Cl (9.9).

EXAMPLE NO. 4

5-(6-Dimethylaminopurin-9yl)-5-desoxy-1.4;3.6-dianhydro-L-iditol 2-nitrate:

(a) 5-(6-Dimethylaminopurin-9-yl)-5-desoxy-1.4;3.6-dianhydro-L-iditol:

A mixture of 8.8 g. (30 mmol) 5-(6-methylmercaptopurin-9-yl)-5-desoxy-1.4;3.6-dianhydro-L-iditol and 50 ml. of 40% aqueous dimethylamine solution is stirred in a closed autoclave for 20 hours at 130°. After cooling and decompressing, one evaporates in a vacuum and recrystallises from 20 ml. ethanol. One obtains 5.68 g. (19.5 mmol) 5-(6-dimethylaminopurin-9-yl)-5-desoxy-1.4;3.6-dianhydro-L-iditol. The analytical sample is recrystallised from toluene.

M.p. 139°-141° $[\alpha]^{25}_D$ 29.5 (c 1; chloroform). Elementary analysis: $C_{13}H_{17}N_5O_3$ (291.31). calc.: C (53.60), H (5.88), N (24.04); found: C (53.90), H (5.97), N (24.11).

(b) The esterification with nitric acid in glacial acetic acid/acetic anhydride takes place analogously to the preceding Example 3c. One obtains from 4.4 g. (15.1 mmol) 5-(6-dimethylaminopurin-9-yl)-5-desoxy-1.4;3.6-dianhydro-L-iditol a total of 3.35 g. (10 mmol) 5-(6-dimethylaminopurin-9-yl)-5-desoxy-1.4;3.6dianhydrol-L-iditol 2-nitrate. The analytical sample is recrystallised from toluene/petroleum ether. M.p. 134°-136° (decomp.) $[\alpha]^{25}_D$ 54.2 (c 0.5; chloroform). Elementary analysis: $C_{13}H_{16}N_6O_5$ (336.31). calc.: C (46.43), H (4.80), N (24.99); found: C (46.38), H (4.89), N (24.69).

A part is converted into the hydrochloride and recrystallised from isopropanol/ethanol.

M.p. 169°-170° (decomp.) $[\alpha]^{25}_D$ 37.5(c 1.1; water) Elementary analysis: $C_{13}H_{16}N_6O_5 \times HCl$ (372.77).

EXAMPLE NO. 5

5-(6-Ethylaminopurin-9-yl)-5-desoxy-1.4;3.6-dianhydro-L-iditol 2-nitrate:

(a) 5-(6-Ethylaminopurin-9-yl)-5-desoxy-1.4;3.6-dianhydro-L-iditol:

A mixture of 8.8 g. (30 mmol) 5-(6-methylmercaptopurin-9-yl)-5-desoxy-1.4;3.6-dianhydro-L-iditol, 8.1 g. (100 mmol) ethylamine hydrochloride, 4.0 g. (100 mmol) sodium hydroxide and 50 ml. water is stirred in a closed autoclave for 20 hours at 130°. After cooling and decompressing, one evaporates to dryness, dissolves the residue in 100 ml. water and extracts 10 times with 100 ml. amounts of chloroform. Evaporation of the chloroform extracts gives 8.15 g. of oily crude product which is converted with 14 ml. 2 molar hydrochloric acid into the hydrochloride, again evaporated and recrystallised from methanol/ether. One obtains 5.7 g. (17.4 mmol) 5-(6-ethylaminopurin-9-yl)-5-desoxy-1.4;3.6-dianhydro-L-iditol hydrochloride.

M.p. 240°-2°; $[\alpha]^{25}_D$ 37.7 (c 1; water). Elementary analysis: $C_{13}H_{17}N_5O_3 \times HCl$ (327.76). calc.: C (47.64), H (5.53), N (21.37), Cl (10.82); found: C (47.78), H (5.61), N (21.40), Cl (10.95).

(b) For the esterification with nitric acid, one converts the previously obtained hydrochloric into the base and then treats, analogously with Example 3c, with nitric acid/glacial acetic acid/acetic anhydride. From 4.4 g. (15.1 mmol) of base one obtains 2.8 g. (7 mmol) 5-(6-ethylaminopurin-9-yl)-5-desoxy-1.4;3.6-dianhydro-L-iditol 2nitrate in the form of the hydrogen nitrate. The analytical sample is recrystallised from methanol.

M.p. 185°-7° (decomp.); $[\alpha]^{25}_D$ 31.7 (c 0.5; water). Elementary analysis: $C_{13}H_{16}H_6O_5 \times HNO_3$ (399.33). calc.: C (39.10), H (4.29), N (24.55); found: C (39.14), H (4.37), N (24.30).

A part is converted into the hydrochloride and recrystallised from isopropanol/ethanol.

M.p. 212°-14° (decomp.); $[\alpha]^{25}_D$ 48.5 (c 1; water). Elementary analysis: $C_{13}H_{16}N_6O_5 \times HCl$ (372.77). calc.: C (41.89), H (4.60), N (22.54), Cl (9.51); found: C (42.08), H (4.60), N (22.61), Cl (9.4).

EXAMPLE NO. 6

5-(6-Pyrrolidinopurin-9-yl)-5-desoxy-1.4;3.6-dianhydro-L-iditol 2-nitrate:

(a) 5-(6-Pyrrolidinopurin-9-yl)-5-desoxy-1.4;3.6-dianhydro-L-iditol:

A mixture of 8.8 g. (30 mmol) 5-(6-methylmercaptopurin-9yl)-5-desoxy-1.4;3.6-dianhydro-L-iditol and 25 ml. (300 mmol) pyrrolidine is stirred for 20 hours in a closed autoclave at 130°. After cooling and decompressing, one distils off excess pyrrolidine, towards the end with the addition of water, and recrystallises the residue from water. One obtains 8.43 g. (26.6 mmol) 5-(6-pyrrolidinopurin-9-yl)-5-desoxy-1.4;3.6-dianhydro-L-iditol.

M.p. 183.5°-185.5°; $[\alpha]^{25}_D$ 34.5 (c 1; chloroform). Elementary analysis: $C_{15}H_{19}N_5O_3$ (317.35). calc.: C (56.77), H (6.03), N (22.07); found: C (57.00), H (6.07), N (22.08).

(b) Esterification with nitric acid:

To a solution of 6.35 g. (20 mmol) of the previously obtained 5-(6-pyrrolidinopurin-9-yl) -5-desoxy-1.4;3.6-dianhydro-L-iditol in 40 ml. acetic acid, one adds 1.2 g. (20 mmol) urea and adds dropwise, with stirring and cooling to about 10°-15°, a solution of 3.5 ml. (80 mmol) 95% nitric acid (d = 1.5) in 20 ml. glacial acetic acid and subsequently also 20 ml. acetic anhydride. One further stirs for 5 hours at 15°-20°, then dilutes with water to a total volume of 270 ml., stirs for 30 min. and adds 6 g. (71 mmol) sodium hydrogen carbonate portionwise thereto. One extracts three times with 100 ml. amounts of chloroform, dries the chloroform extracts with anhydrous sodium sulphate and sodium carbonate and evaporates in a vacuum at about 40°-50°. The residue is dissolved in 100 ml. ether; by the addition of petroleum ether, one precipitates out by-products as an oily precipitate. One decants off from the precipitate and adds further petroleum ether thereto, whereby the pure product slowly crystallises out. One obtains 5.53 g. (15.3 mmol) 5-(6-pyrrolidinopurin-9-yl)-5-desoxy-1.4;3.6-dianhydro-L-iditol 2-nitrate. The analytical sample is recrystallised from tioluene/petroleum ether.

M.p. 146°-7°; $[\alpha]^{25}_D$ 58.4 (c 0.48; chloroform). Elementary analysis: $C_{15}H_{18}N_6O_5$ (362.35). calc.: C (49.72), H (5.01), N (23.19); found: C (49.73), H (5.08), N (23.04).

A part is converted into the hydrochloride and reprecipitated from isopropanol/ether.

M.p. 189°-196° (decomp.); $[\alpha]^{25}_D$ 44.7 (c 0.53; water). Elementary analysis: $C_{15}H_{18}N_6O_5 \times HCl$ (398.81). calc.: C (45.18), H (4.80), N (21.07), Cl (8.89); found: C (45.20), H (4.83), N (21.17), Cl (9.1).

EXAMPLE NO. 7

5-(6-Piperidinopurin-9-yl)-5-desoxy-1.4;3.6-dianhydro-L-iditol 2-nitrate:

(a) 5-(6-Pipetridinopurin-9-yl)-5-desoxy-1.4;3.6-dianhydro-L-iditol:

Analogously to the previous Example, 8.8 g. (30 mmol) 5-(6-methylmercaptopurin-9-yl)-5-desoxy-1.4;3.6-dianhydro-L-iditol are stirred together with 25 ml. (253 mmol) piperidine for 20 hours at 130° in a closed autoclave. After distilling off the excess piperidine (towards the end, with the addition of water), one triturates the oily residue with toluene. The now solid crude product is filtered off with suction, dried and recrystallised from water. One obtains 7.7 g. (23.2 mmol) pure 5-(6-piperidinopurin-9-yl)-5-desoxy-1.4;3.6-dianhydro-L-iditol.

M.p. 136°-139°; $[\alpha]^{25}_D$ 30.1 (c 1; chloroform). Elementary analysis: $C_{16}H_{21}N_5O_3$ (331.38). calc.: C (57.99), H (6.39), N (21.13); found: C (58.14), H (6.48), N (21.13).

(b) The esterification of the above-described product with nitric acid and glacial acetic acid/acetic anhydride takes place analogously to Example 6 b. From 5.0 g. (15 mmol) one obtains, after crystallisation from ether/petroleum ether, 2.17 g. (5.8 mmol) 5-(6-piperidinopurin-9-yl)-5-desoxy-1.4;3.6-dianhydro-L-iditol 2-nitrate. The analytical sample is recrystallised from toluene/petroleum ether.

M.p. 115°-117°; $[\alpha]^{25}_D$ 58.1 (c 1; chloroform). Elementary analysis: $C_{16}H_{20}N_6O_5$ (376.38). calc.: C (51.06), H (5.36), N (22.33); found: C (50.98), H (5.47), N (22.20).

A part of the product is converted into the hydrochloride and reprecipitated from isopropanol/ether.

M.p. 179°-184° (decomp.); $[\alpha]^{25}_D$ 58 (c 0.5; methanol). Elementary analysis: $C_{16}H_{20}N_6O_5 \times HCl$ (412.84). calc.: C (46.55), H (5.13), N (20.36), Cl (8.59); found: C (46.68), H (5.22), N (20.43), Cl (8.6).

EXAMPLE NO. 8

5-(6-Morpholinopurin-9-yl)-5-desoxy-1.4;3.6-dianhydro-L-iditol 2-nitrate:

(a) 5-(6-Morpholinopurin-9-yl)-5-desoxy-1.4;3.6-dianhydro-L-iditol:

Analogously to the above Examples 6 a and 7 a, one obtains from 8.8 g. (30 mmol) 5-(6-methylmercaptopurin-9-yl)-5-desoxy-1.4;3.6-dianhydro-L-iditol and 25 ml. (287 mmol) morpholine, after stirring for 20 hours at 130° in a closed autoclave, distilling off the excess morpholine, with the addition of water, and recrystallisation of the residue from water, 6.9 g. (18.7 mmol) pure 5-(6-morpholinopurin-9-yl)-5-desoxt-1.4;3.6-dianhydro-L-iditol in the form of the dihydrate.

M.p. 84°–88°; $[\alpha]^{25}_D$ 26.4 (c 1; chloroform). Elementary analysis: $C_{15}H_{19}N_5O_4 \times 2H_2O$ (369.38). calc.: C (48.78), H (6.28), N (18.96); found: C (48.71), H (6.31), N (18.74)

(b) Esterification with nitric acid:

Analogously to Examples 6 b and 7 b, one obtains from 5.5 g. (14.5 mmol) of the above-described dihydrate, by treatment with 95% nitric acid in glacial acetic acid/acetic anhydride and recrystallisation of the crude product from a little ethanol, 3.65 g. (9.6 mmol) 5-(6-morpholinopurin-9-yl)-5-desoxy-1.4;3.6-dianhydro-L-iditol 2-nitrate. The analytical sample is again recrystallised from toluene/ether.

M.p. 173°–5°; $[\alpha]^{25}_D$ 53.8 (c 1; chloroform). Elementary analysis: $C_{15}H_{18}N_6O_6$ (378.35). calc.: C (47.62), H (4.79), N (22.21); found: C (48.16), H (4.92), N (21.72).

A part of the product is converted into the hydrochloride and reprecipitated from isopropanol/ether.

M.p. 187°–9° (decomp.); $[\alpha]^{25}_D$ 55.0 (c 0.51; methanol). Elementary analysis: $C_{15}H_{18}N_6O_6 \times HCl$ (414.81). calc.: C (43.43), H (4.62), N (20.26), Cl (8.55); found: C (44.20), H (4.72), N (20.25), Cl (8.1).

EXAMPLE NO. 9

5-[6-(4-Methylpiperazino)-purin-9-yl]-5-desoxy-1.4;3.6-dianhydro-L-iditol 2-nitrate:

(a) 5-[6-(4-Methylpiperazino)-purin-9-yl]-5-desoxy-1.4;3.6-dianhydro-L-iditol:

Analogously to the preceding Examples, one obtains from 8.8 g. (30 mmol) 5-(6-methylmercaptopurin-9-yl)-5-desoxy-1.4;3.6-dianhydro-L-iditol and 25 ml. (225 mmol) N-methypiperazine, 10.2 g. (29.4 mmol) of crude product. Recrystallisation from toluene gives 6.3 g. (18.2 mmol) of pure product.

M.p. 166°–7°; $[\alpha]^{25}_D$ 31.1 (c 1; chloroform). Elementary analysis: $C_{16}H_{22}N_6O_3$ (346.40). calc.: C (55.48), H (6.40), N (24.26); found: C (55.60), H (6.45), N (23.91).

(b) The esterification with nitric acid is carried out analogously to the preceding Examples. After recrystallisation from ether, one obtains 5-[6-(4-methylpiperazino)-purin-9-yl]-5-desoxy-1.4;3.6-dianhydro-L-iditol 2-nitrate.

M.p. 107°–9°; $[\alpha]^{25}_D$ 62.1 (c 0.53; chloroform). Elementary analysis: $C_{16}H_{21}N_7O_5$ (391.40). calc.: C (49.10), H (5.41), N (25.05); found: C (49.40), H (5.59), N (24.93).

A part of the product is mixed with 2 equivalents of hydrochloric acid, evaporated in a vacuum and recrystallised from ethanol/isopropanol. One obtains the dihydrochloride hydrate.

M.p. 173°–80° (decomp.); $[\alpha]^{25}_D$ 32 (c 1; water). Elementary analysis: $C_{16}H_{21}N_7O_5 \times 2HCl \times H_2O$ (482.34). calc.: C (39.84), H (5.22), N (20.33), Cl (14.70); found: C (40.39), H (5.39), N (20.50), Cl (14.6). EXAMPLE NO. 10

5-[9-(6-N-Pivaloyl)-adenyl]-5-desoxy-1.4;3.6-dianhydro-L-iditol 2-nitrate:

A solution of 3.1 g. (10 mmol) 5-(9-adenyl)-5-desoxy-1.4;3.6-dianhydro-L-iditol 2-nitrate and 7 ml. (50 mmol) triethylamine in 80 ml. anhydrous dioxan is mixed, with stirring and the exclusion of moisture, with 6.1 ml. (50 mmol) pivaloyl chloride. One heats under reflux for 1 hour, allows to cool and filters off with suction precipitated triethylamine hydrochloride. The filtrate is evaporated to a volume of about 30 ml. and stirred into 100 ml. ice water. The deposited oily precipitate is separated off and the aqueous phase extracted with 50 ml. chloroform. Precipitate and chloroform extract are combined; from the so obtained solution one precipitates out the crude product with petroleum ether. Reprecipitation of the crude product from chloroform/petroleum ether, followed by recrystallisation from ethanol, gives 1.83 g. (4.7 mmol) 5-[9-(6-N-pivaloyl)-adenyl]-1.4;3.6-dianhydro-L-iditol 2-nitrate.

M.p. 171°–3°; $[\alpha]^{25}_D$ 35.8 (c 0.95; chloroform). Elementary analysis: $C_{16}H_{20}N_6O_6$ (392.38). calc.: C (48.98), H (5.14), N (21.42); found: C (48.96), H (5.24), N (20.61).

EXAMPLE NO. 11

5-[9-(6-N-Acetyl)-adenyl]-5-desoxy-1.4;3.6-dianhydro-L-iditol 2-nitrate:

The product is obtained analogously to Example No. 10 by acetylation of 5-(9-adenyl)-5-desoxy-1.4;3.6-dianhydro-L-iditol 2-nitrate. After recrystallisation from methanol/ether, it has the m.p. 158°–161° and $[\alpha]^{25}_D$ 35 (c 1; chloroform).

$C_{13}H_{14}N_6O_6$ (350.29).

EXAMPLE NO. 12

5-(7-Theophyllinyl)-5-desoxy-1.4;3.6-dianhydro-L-iditol 2-nitrate:

(a) 5-(7-Theophyllinyl)-5-desoxy-1.4;3.6-dianhydro-L-iditol:

A mixture of 44.8 g. (0.2 mol) 1.4;3.6-dianhydro-D-glucitol 5-methanesulphonate, 80.8 g. (0.4 mol) theophyllin sodium sat and 600 ml. dimethyl sulphoxide is stirred for 48 hours under an atmosphere of nitrogen at 130°. One distils off the dimethyl sulphoxide in vacuo, dissolves the residue in 400 ml. hot water, after cooling extracts twice with 200 ml. amounts of chloroform and shakes out the chloroform extracts with 200 ml. water. The combined aqueous phases are boiled up with 30 g. active charcoal, filtered and the filtrate, after neutralisation, evaporated to dryness. The residue is stirred with 1 liter of ethanol, filtered and again evaporated. For the removal of residual theophyllin, one dissolves in 700 ml. 2% aqueous sodium hydroxide solution and extracts the reaction product continuously with chloroform. The chloroform extract gives, after drying over anhydrous sodium sulphate and evaporation, 27.5 g. (89 mmol) 5-(7-theophyllinyl)-5-desoxy-1.4;3.6-dianhydro-L-iditol. The analytical sample is recrystallised from acetone/ethanol.

M.p. 196°–8°; $[\alpha]^{25}_D$ —27.9 (c 0.5; water). Elementary analysis: $C_{13}H_{16}N_4O_5$ (308.30). calc.: C (50.65), H (5.23), N (18.17); found: C (50.68), H (5.32), N (18.06).

(b) Esterification with nitric acid:

To 150 ml. 95% nitric acid (d=1.5), one adds in small portions, with stirring and cooling to —15°, first 10.8 g. (180 mmol) urea and subsequently, also in small portions, a total of 17.45 g. (56.6 mmol) of the above-described 5-(7-theophyllinyl)-5-desoxy-1.4;3.6-dianhydro-L-iditol. One then stirs for 1 hour at —15°, dilutes with 850 ml. water, adds thereto a solution of 130 g. (3.25 mol) sodium hydroxide in 1 liter water and renders neutral by the addition of sodium hydrogen carbonate. The product is obtained as a precipitate; one filters off with suction, washes with 100 ml. water and dissolves the precipitate in 1 liter chloroform. After drying over anhydrous sodium sulphate, filtering and evaporating the chloroform solution, one recrystallises from acetone/methanol and obtains 14.5 g. (41 mmol) 5-(7-theophyllinyl)-5-desoxy-1.4;3.6-dianhydro-L-iditol 2 -nitrate.

M.p. 193°; $[\alpha]^{25}_D$ 22.9 (c 0.5; dimethylformamide) Elementary analysis: $C_{13}H_{15}N_5O_7$ (353.29) calc.: C (44.20), H (4.28), N (19.82) found: C (44.07), H (4.27), N (19.58)

EXAMPLE NO. 13

5-(6-Benzylaminopurin-9-yl)-5-desoxy-1.4;3.6-dianhydro-L-iditol 2-nitrate:
(a) 5-(6-Benzylaminopurin-9-yl)-5-desoxy-1.4;3.6-dianhydro-L-iditol:

A mixture of 8.8 g. (30 mmol) 5-(6-methylmercaptopurin-9-yl)-5-desoxy-1.4;3.6-dianhydro-L-iditol and 25 ml. (229 mmol) benzylamine is stirred in a closed autoclave for 20 hours at 130° . After cooling and decompressing, one distils off the excess benzylamine—towards the end, with the addition of water—in vacuo, recrystallises the oily residue from acetone and obtains 6.9 g. (19.5 mmol) 5-(6-benzylaminopurin-9-yl)-5-desoxy-1.4;3.6-dianhydro-L-iditol. The analytical sample is again recrystallised from toluene.

M.p. 151°-3°; $[\alpha]^{25}_D$ 28.7 (c 1; chloroform). Elementary analysis: $C_{18}H_{19}N_5O_3$ (353.38). calc.: C (61.18), H (5.42), N (19.82); found: C (61.17), H (5.44), N (19.82).
(b) Esterification with nitric acid:

To a mixture of 5.3 g. (15 mmol) of the abovedescribed 5-(6-benzylaminopurin-9-yl)-5-desoxy-1.4;3.6-dianhydro-L-iditol, 0.9 g. (15 mmol) urea and 60 ml. acetic acid, one adds dropwise, with stirring and cooling to 10°, a solution of 2.5 ml. (60 mmol) 95% nitric acid (d=1.5) in 15 ml. acetic acid and thereafter 15 ml. acetic anhydride. One further stirs for 3 hours at 10°, adds 350 ml. of water thereto, stirs for 30 min. and then adds 5 g. sodium hydrogen carbonate thereto. The crude product is obtained as a precipitate, which is filtered off with suction, dried and recrystallised from benzene/ether/petroleum ether. One obtains 4.05 g. (about 10 mmol) of crystallisate, which consists of a mixture of free base and hydrogen nitrate of 5-(6-benzylaminopurin-9-yl)-5-desoxy-1.4;3.6-dianhydro-L-iditol 2-nitrate. A part thereof is dissolved in glacial acetic acid, mixed with just about the equimolar amount of nitric acid, the hydrogen nitrate which crystallises out is filtered off with suction and recrystallised from methanol.

M.p. 109°-110°; $[\alpha]^{25}_D$ 57.9 (c 0.54; chloroform). Elementary analysis: $D_{18}H_{18}N_6O_5 \times HNO_3$ (461.40). calc.: C (46.86), H (4.15), N (21.25); found: C (46.56), H (4.20), N (21.08).

A further part is first converted into the free base, then into the hydrochloride with hydrochloric acid and recrystallised from ethanol/methanol.

M.p. 193°-201° (decomp.); $[\alpha]^{25}_D$ 52.7 (c 1; methanol). Elementary analysis: $C_{18}H_{18}N_6O_5 \times HCl$ (434.84). calc.: C (49.72), H (4.40), N (19.33), Cl (8.15); found: C (49.82), H (4.40), N (19.36), Cl (8.2);

EXAMPLE NO. 14

5-[6-(3-Phenylpropyl)-aminopurin-9-yl]-5-desoxy-1.4;3.6-dianhydro-L-iditol 2-nitrate:
(a) 5-[6-(3-Phenylpropyl)-aminopurin-9-yl]-5-desoxy-1.4;3.6-dianhydro-L-iditol:

A mixture of 19.1 g. (65 mmol) 5-(6-methylmercaptopurin-9-yl)-5-desoxy-1.4;3.6-dianhydro-L-iditol and 94 ml. (650 mmol) 3-phenylpropylamine is heated in a closed steel autoclave for 36 hours at 150° . After cooling and decompressing, one adds thereto 80 ml. acetic acid and 500 ml. water and extracts twice with 300 ml. amounts of chloroform. The chloroform extracts are washed with 300 ml. water and extracted twice with a solution of 25 ml. 37% hydrochloric acid in 200 ml. water. The hydrochloric acid extracts are rendered alkaline with aqueous sodium hydroxide solution, and extracted with 400 ml. dichloromethane. The dichloromethane extract gives, after drying over anhydrous sodium sulphate, filtering and evaporating, 20 g. (52.4 mmol) of crude base which is dissolved, with warming, in 150 ml. isopropanol and mixed with 15 ml. 37% hydrochloric acid (180 mmol). Upon cooling, 18.8 g. (41.4 mmol) of pure product crystallise out in the form of the dihydrochloride.

M.p. 159°-62°; $[\alpha]^{25}_D$ 30.6 (c 0.4; water). Elementary analysis: $C_{20}H_{23}N_5O_3 \times 2HCl$ (454.36). calc.: C (52.86), H (5.55), N (15.41), Cl (15.61); found: C (53.23), H (5.55), N (15.41), Cl (14.4).
(b) Esterification with nitric acid:

To a mixture of 11.4 g. (30 mmol) 5-[6-(3-phenylpropyl)-aminopurin-9-yl]-5-desoxy-1.4;3.6-dianhydro-L-iditol (obtained from the previously described dihydrochloride), 1.8 g. (30 mmol) urea and 120 ml. glacial acetic acid, one adds dropwise, with stirring and cooling to 10°-15°, a solution of 5.2 ml. (120 mmol) 96% nitric acid (d=1.5) in 30 ml. glacial acetic acid and subsequently 30 ml. acetic anhydride, then stirs for 8 hrs. at 15°-20°, dilutes with 800 ml. water and leaves to stand overnight. After the addition of 75 ml. 2 molar aqueous sodium hydroxide solution, one stirs up thoroughly, extracts 2 times with 500 ml. amounts of chloroform, washes the combined chloroform extracts free of acid with dilute aqueous sodium hydroxide solution, dries over anhydrous sodium sulphate, filters and evaporates under reduced pressure. One obtains 11.8 g. (about 25 mmol) of crude product which is contaminated by product nitrated on the phenyl radical. For purification, one converts into the hydrochloride in ethanolic solution with 27 mmol hydrochloric acid, again evaporates, extracts the by-products at boiling temperature with chloroform and recrystallises the insoluble main product from ethanol/chloroform and from ethanol. The so obtained 5-[6-(3-phenylpropyl)-aminopurin-9-yl]-5-desoxy-1.4;3.6-dianhydro-L-iditol 2-nitrate hydrochloride has the m.p. 200°-203° (decomp.); $[\alpha]^{25}_D$ 41.2 (c 0.21; dimethylformamide).

Yield: 4.84 g. (10.5 mmol). Elementary analysis: $C_{20}H_{22}N_6O_5 \times HCl$ (462.89). calc.: C (51.90), H (5.01), N (18.16), Cl (7.66); found: C (52.00), H (5.07), N (18.26), Cl (8.0).

EXAMPLE NO. 15

2-(9-Adenyl)-2-desoxy-1.4;3.6-dianhydro-D-glucitol 5-nitrate:
(a) 1.4;3.6-Dianhydro-D-mannitol 2-methanesulphonate:

To a solution of 877 g. (6 mol) 1.4;3.6-dianhydro-D-mannitol in 6 liters of pyridine, one adds dropwise, with stirring and exclusion of moisture, as well as cooling to −15°, within 6 hrs., 525 ml. (6.6 mol) methanesulphonyl chloride, further stirs for 3 days at −15° and then distils off the pyridine under reduced pressure. Upon mixing the oily residue with 2.7 liters of water, pure 1.4;3.6- dianhydro-D-mannitol 2,5-dimethanesulphonate crystallises out, which is separated off and washed 2 times with 700 ml. amounts of water. The combined filtrates are mixed with a solution of 264 g. (6.6 mol) sodium hydroxide in 2.5 liters of water, adjusted to pH=7 by the addition of sodium hydrogen carbonate, evaporated under reduced pressure and dried azeotropically with chloroform. The residue is hot extracted twice with 2.5 liter amounts of chloroform and filtered. The combined chloroform extracts are extracted 5 times with 1 liter amounts of water. Upon concentration of the aqueous phases, the 1.4;3.6-dianhydro-D-mannitol 2-methanesulphonate crystallises out. The mother liquor remaining after the suction filtration gives further product after evaporation and recrystallisation from ethanol. Residual product is obtained by evaporation of the ethanolic mother liquor, dissolving of the residue in water and continuous extraction of the aqueous solution with chloroform in a rotary percolator. Unreacted 1.4;3.6-dianhydro-D-mannitol remains in the aqueous phase. In all, one obtains 396 g. (1.77 mol) 1.4;3.6-dianhydro-D-mannitol 2-methanesulphonate (besides 465 g.=1.54 mol of the dimethanesulphonate). The analytical sample has, after recrystallisation from chloroform, the m.p. 111°–112° and $[\alpha]^{25}_D$ 118 (c 1.0; acetone).

Elementary analysis: $C_7H_{12}O_6S$ (224.24). calc.: C (37.50), H (5.40), S (14.30); found: C (37.41), H (5.59), S (13.7).

(b) 2-(9-Adenyl)-2-desoxy-1.4;3.6-dianhydro-D-glucitol:

A mixture of 112 g. (0.5 mol) 1.4;3.6-dianhydro-D-mannitol 2-methanesulphonate, 86 g. (0.55 mol) adenine sodium salt and 1500 ml. anhydrous dimethyl sulphoxide is stirred for 1 day at 100°. One distils off the solvent under reduced pressure as far as possible, mixes the residue with 4.5 liters of water and extracts continuously with chloroform for 2 days in a 5 l. rotary perforator (Normag). The crude product crystallises out from the chloroform phase which, after recrystallisation from ethanol/water, gives 6.9 g. (26.2 mmol) of pure product. The filtrate is combined with the aqueous phase of the percolation and concentrated to about 100 ml. A further 21.3 g. (80.9 mmol) of product crystallise out.

Total yield: 28.2 g. (107 mmol) M.p. (ethanol/water): 265°–7°; $[\alpha]^{25}_D$ 20.8 (c 1.0; water). Elementary analysis: $C_{11}H_{13}N_5O_3$ (263.25). calc.: C (50.19), H (4.98), N (26.20); found: C (49.97), H (5.04), N (26.80).

About 40% of unreacted 1.4;3.6-dianhydro-D-mannitol 2-methanesulphonate can be recovered from the chloroform phase of the perforation.

(c) 2-(9-Adenyl)-2-desoxy-1.4;3.6-dianhydro-D-glucitol 5-nitrate:

With stirring and cooling to $-20°$, one adds a solution of 4 g. (67 mmol) urea in 170 ml. conc. sulphuric acid (d=1.84; about 3 mol) dropwise to 60 ml. of 96% nitric acid (d=1.5; 1.37 mol) and subsequently a solution of 21 g. (80 mmol) 2-(9-adenyl)-2-desoxy-1.4;3.6-dianhydro-D-glucitol in 12 ml. water +30 ml. methanesulphonic acid and then stirs at $-20°$ for one hour. One pours the mixture into 1 liter of ice water and adds dropwise thereto, with stirring, a solution of 300 g. (7.5 mol) sodium hydroxide in 1 liter of water. By the addition of aqueous sodium hydrogen carbonate, one completes the neutralisation and extracts the mixture 4 times with 1.5 liter amounts of chloroform. The combined chloroform phases give, after drying over anhydrous sodium sulphate, filtering and evaporating under reduced pressure, 16.8 g. (54.5 mmol) of crude base. This is converted into the hydrochloride and gives, after recrystallisation from methanol, 16.3 g. (47.3 mmol) 2-(9-adenyl)-2-desoxy-1.4;3.6-dianhydro-D-glucitol 5-nitrate hydrochloride.

M.p. (from water): 214°–5° (decomp.); $[\alpha]^{25}_D$ 62.6 (c 0.5; water). Elementary analysis: $C_{11}H_{12}N_6O_5 \times HCl$ (344.71). calc.: C (38.33), H (3.80), N (24.38), Cl (10.28); found: C (38.21), H (3.59), N (24.46), Cl (10.3).

EXAMPLE NO. 16

5-{6-[3-(4-Chlorophenyl)-propylamino]-purin-9-yl}-5-desoxy-1.4;3.6-dianhydro-L-iditol 2-nitrate:

(a) 5-{6-[3-(4-Chlorophenyl)-propylamino]-purin-9-yl}-5-desoxy-1.4;3.6-dianhydro-L-iditol:

Preparation analogous to Example 14 a by the reaction of 3-(4-chlorophenyl)-1-aminopropane with 5-(6-methylmercaptopurin-9-yl)-5-desoxy-1.4;3.6-dianhydro-L-iditol. After conversion into the hydrochloride and recrystallisation from 96% ethanol, one obtains, in 80% yield, the pure product in the form of the hydrochloride hemihydrate with m.p. 116°–120° and $[\alpha]^{25}_D$ 39 (c 0.4; ethanol).

Elementary analysis: $C_{20}H_{22}ClN_5O_3 \times HCl \times 0.5\ H_2O$ (461.35). calc.: C (52.07), H (5.24), N (15.18), Cl (15.37); found: C (52.34), H (5.20), N (15.15), Cl (15.5).

(b) Esterification with nitric acid:

Analogously to Example 14 b. After conversion into the hydrochloride and recrystallisation twice from methanol/water, one obtains, in 24% yield, pure 5-{6-[3-(4-chlorophenyl)-propylamino]-purin-9-yl}-5-desoxy-1.4;3.6-dianhydro-L-iditol 2-nitrate hydrochloride with the m.p. 183°–185° (decomp.) and $[\alpha]^{25}_D$ 42.5 (c 0.2; ethanol).

Elementary analysis: $C_{20}H_{21}ClN_6O_5 \times HCl$ (497.35). calc.: C (48.30), H (4.46), N (16.90), Cl (14.26); found: C (48.38), H (4.46), N (16.72), Cl (14.1).

In the investigation of the pharmacological properties of the compounds according to the invention, as comparison compounds there were always used the commercially available compounds isosorbide dinitrate (ISDN) and isosorbide mononitrate (ISMN), whereby, in the case of ISMN, it is 1.4;3.6-dianhydro-D-glucitol 2-nitrate.

The coronary flowthrough-increasing effectiveness of the compounds according to the invention was determined on isolated guinea pig hearts (isolated hearts according to Langendorff, Method according to Bunger et el.; Pflüger's Archiv. 353, 317–325 (1975)). After reaching the stationary state in the 30th minute, the hearts were infused in each case with 50 ml. of tyrode solution with a content of test substance of, in each case, 25 μg./ml. Each test substance was tested on 3–6 hearts.

In each case, there were measured the inotropism, the throughflow and the frequency, whereby the values given in Table I are average values of the percentage change in comparison with the initial values. The comparison of the measured values shows that the coronary flowthrough-increasing effectiveness of the compounds according to the invention is greater than that of ISMN; the coronary flowthrough-increasing effectiveness of some compounds even exceeds that of ISDN.

TABLE I

Experiments on Langendorff hearts

| Substance compound according to Example | dose (μg/ml) | In-otropism | Flow-through | Fre-quency | Remarks |
|---|---|---|---|---|---|
| 1c or 2c | 25 | −8.97 | +92.13 | +4.92 | |
| 3c | 25 | −4.74 | +39.88 | +0.60 | |
| 4b | 25 | −7.49 | +103.37 | −4.92 | |
| 5b | 25 | −6.10 | +66.97 | −1.54 | |
| 6b | 25 | −12.96 | +23.94 | +0.15 | |
| 9b | 25 | −5.15 | +35.93 | −7.58 | |
| 12b | 25 | 0 | +11.43 | +7.84 | |
| ISDN | 25 | −8.11 | +91.54 | +2.00 | comparison |
| ISMN | 25 | −2.67 | +9.11 | −0.51 | compounds |

The spasmolytic effectiveness of the compounds according to the invention was determined on isolated rat aorta preparations with noradrenaline-induced and potassium chloride-induced contractions (method according to Wende and Peiper, Pflüger's Archiv, 320, 133–141 (1970); and Towart and Stoepel, Naunyn-Schmiedeberg's Archives of Pharmacology; Suppl. Vol., 308, R 18 (1979)).

In Table II are given the concentrations of the test substances which are necessary for a 50% inhibition of the spasm ($ED_{50}$ values). The spasmolytic effectivenesses of the compounds according to the invention are quite preponderantly better than those of ISMN and ISDN, especially when one takes into account the pharmacologically important relationship of the effective doses in the case of noradrenaline spasm and potassium chloride spasm.

TABLE II

$ED_{50}$ values for spasmolytic actions

| Substance compound according to Example | Noradrenaline spasm (Mol/l.) | Potassium chloride spasm (Mol/l.) |
|---|---|---|
| 1c or 2c | $1.35 \times 10^{-7}$ | $2.80 \times 10^{-6}$ |
| 3c | $4.80 \times 10^{-7}$ | $4.60 \times 10^{-6}$ |
| 4b | $2.20 \times 10^{-7}$ | $2.90 \times 10^{-5}$ |
| 5b | $3.80 \times 10^{-7}$ | $1.30 \times 10^{-5}$ |
| 6b | $5.40 \times 10^{-7}$ | $4.07 \times 10^{-6}$ |
| 7b | $2.40 \times 10^{-7}$ | $2.90 \times 10^{-6}$ |
| 8b | $2.90 \times 10^{-7}$ | $3.00 \times 10^{-6}$ |
| 9b | $2.65 \times 10^{-6}$ | $2.50 \times 10^{-5}$ |
| 10 | $3.02 \times 10^{-7}$ | $6.50 \times 10^{-6}$ |
| 12b | $3.20 \times 10^{-6}$ | $4.20 \times 10^{-6}$ |
| 13b | $1.68 \times 10^{-8}$ | $2.40 \times 10^{-6}$ |
| ISDN (comparison) | $1.30 \times 10^{-6}$ | $3.10 \times 10^{-6}$ |
| ISMN (comparison) | $1.60 \times 10^{-5}$ | $2.40 \times 10^{-6}$ |

The blood pressure-lowering effectiveness of the compounds according to the invention on narcotised guinea pigs after intravenous administration was measured. The values given in Table III show that the compounds according to the invention are substantially more effective than ISMN, whereby the adenyl derivative of 1.4;3.6-dianhydro-iditol mononitrate (compound according to Example 1c/2c) is even more effective than ISDN.

The heart-circulation effectiveness of the compounds according to the invention was determined on mongrel cats of 2.5 to 3.5 kg. body weight by intraduodenal administration. The animals were narcotised with a mixture of chloralose-urethane (1.2 g./kg. urethane + 40 mg./kg. chloralose administered i.p.). They breathed spontaneously through a tracheal canula. The A. carotis sinistra was used in order to place a catheter tip monometer in the left chamber of the heart. The V. jugularis served for injection purposes. Via the A. femoralis dextra, a catheter was inserted up into the Aorta descendans and connected to a pressure recorder (Statham P 23Db). The heart frequency was recorded with a pulse frequency measurer (Firm Hugo Sachs Elektronik) from the left ventricular pressure signal. A duodenal loop was exposed by laparotomy. The substances to be tested were injected directly into the lumen. As follows from the values given in Table IV, the degree of blood pressure lowering in the case of the compounds according to the invention is significantly higher and, in particular, longer lasting than in the case of the comparison compounds ISMN and ISDN. This means that the compounds according to the invention are gentle on the heart and possess a lesser negative inotropic action than the comparison compounds.

The circulatory-pharmacological effectiveness of the compounds according to the invention was determined on the narcotised dog with intravenous administration. The investigations were carried out on mongrel dogs of both sexes, body weight 20.5 to 29 kg. After a twelve hour fasting period, the animals received 2 mg./kg. morphine s.c. on the morning of the test day. About 30 minutes thereafter, narcosis was induced with 25 mg./kg. nembutal i.v. and maintained by continuous infusion with 5 mg./kg./h. The animals were aerated constantly through a tracheal tube with an $N_2O/O_2$ mixture (2:1). The $CO_2$ of the expired air was measured continuously, the pH value of the blood about every 20 minutes.

For the continuous measurement of the arterial blood pressure, the Arteria saphena dextra was exposed, the Arteria femoralis sinistra for the application of a Statham flow measurement head. From the Arteria brachialis sinistra, a thermoprobe was pushed into the aortal arch; it served for the measurement of the heart minute volume by means of the thermodilution method. With X-ray monitoring, a catheter tip manometer was introduced through the Arteria carotis dextra into the left ventricle and the left ventricular end diastolic pressure determined with it. From the right Vena jugularis, a double-lumen catheter was introduced into the Arteria pulmonalis; via one lumen, an icecooled isotonic NaCl solution was injected for the determination of the heart minute volume, via the other the blood pressure in the Arteria pulmonalia was measured. Through one vein of the left front paw, a catheter was pushed into the right atrium for pressure meaurement. With a differentiator, from the pressure in the left ventricle there was calculated the rate of pressure increase ("dp/dt") as a measure of the contractability. After completion of the preparation, the animals were anti-coagulated with 500 IU/kg. heparin.

After a stabilisation period of about 30 minutes, the heart minute volume was determined. Groups of four animals then each received 1 mg./kg. ISDN or of 1c/2c administered i.v. The parameters of heart frequency, arterial blood pressure, pulmonalis pressure, pressure in the right atrium, left ventricular pressure, dp/dt and average femoralis flow were continuously recorded with a Beckmann 8-channel recorder. Further measurements took place after the 2nd, 5th, 7th, 10th, 20th, 25th, 30th, 40th, 50th, 60th, 120th, 150th and 180th minute. All flow values and values derived therefrom were referred to a body weight of 20 kg. Heart capacities and resistances were calculated in the usual manner.

As follows from the values given in Tables V (circulatory pharmacological effects of the comparison compound ISDN) and VI (circulatory pharmacological effects of the compound 1c/2c according to the invention), the effectiveness of the compound according to the invention is better than that of the comparison compound ISDN, especially with regard to the lowering of the end diastolic pressure in the left ventricle and the longterm lowering of the pressure in the A. pulmonalis.

Legends to Tables V and VI:

Circulatory pharmacological effects of ISDN (Tab. V) and 1c/2c (Tab. VI) on the dog after intravenous administration (1 mg./kg.). Average values and standard errors from groups of 4 animals before the administration (v) or at various times (in min.) after the administration. HF: heart frequency (min$^{-1}$); $AP_{syst.}$, $AP_{diast.}$: systolic and diastolic aorta pressure (mm.Hg); PRA: pressure in the right atrium (mm.Hg); $\overline{PAP}$: average pressure in the A. pulmonalis (mm.Hg); LVEDP: end diastolic pressure in the left ventricle (mm.Hg); dp/dt: rate of pressure increase in the left ventricle (mm.Hg/sec.); $HL_L$: heart capacity left, referred to 20 kg. body weight (W); $HL_R$: heart capacity right, referred to 20 kg. body weight (mW); SV: beat volume, referred to 20 kg. body weight (ml.); $BF_{Fem}$: blood flow in the A. femoralis, referred to 20 kg. body weight (ml./min.); $W_{Fem}$: femoralis resistance, referred to 20 kg. body weight (KU); HZV: heart minute volume, referred to 20 kg. body weight (1/min.); $W_{AP}$: pulmonalis resistance, referred to 20 kg. body weight (U); $W_{TP}$: total peripheral resistance, referred to 20 kg. body weight (U).

TABLE III

Blood pressure experiments on guinea pigs

| substance | dose mg/kg | blood pressure previously mm. Hg | blood pressure afterwards mm. Hg | Δ mm. Hg |
|---|---|---|---|---|
| ISDN | 0.25 | 68.70 ± 2.30 | 57.00 ± 2.10 | −11.70 |
|  | 1.00 | 66.00 ± 3.50 | 46.30 ± 0.90 | −19.70 |
|  | 2.50 | 66.70 ± 1.70 | 37.70 ± 0.90 | −29.00 |
| ISMN | 0.25 | 57.60 ± 3.10 | 53.90 ± 3.10 | −3.70 |
|  | 1.00 | 54.70 ± 3.80 | 48.40 ± 3.20 | −6.30 |
|  | 2.50 | 52.30 ± 4.80 | 41.40 ± 3.90 | −10.90 |
| 1c/2c | 0.25 | 68.25 ± 2.50 | 50.50 ± 2.33 | −17.75 |
|  | 1.00 | 69.50 ± 2.90 | 41.50 ± 3.97 | −28.00 |
|  | 2.50 | 70.00 ± 2.27 | 38.75 ± 2.66 | −31.25 |
| 3c | 0.25 | 79.50 ± 2.50 | 79.25 ± 2.56 | −0.25 |
|  | 1.00 | 79.50 ± 2.66 | 71.50 ± 3.97 | −8.00 |
|  | 2.50 | 77.00 ± 2.80 | 61.50 ± 3.23 | −15.50 |
| 4b | 0.25 | 73.75 ± 2.14 | 63.25 ± 4.23 | −10.50 |
|  | 1.00 | 74.00 ± 1.91 | 59.00 ± 1.47 | −15.00 |
|  | 2.50 | 72.00 ± 2.45 | 43.50 ± 2.50 | −28.50 |
| 5b | 0.25 | 76.50 ± 2.66 | 71.00 ± 5.04 | −5.50 |
|  | 1.00 | 78.50 ± 1.70 | 65.75 ± 3.75 | −12.75 |
|  | 2.50 | 76.25 ± 2.59 | 51.00 ± 3.13 | −25.25 |
| 6b | 0.25 | 65.00 ± 4.02 | 51.50 ± 4.94 | −13.50 |
|  | 1.00 | 65.50 ± 2.36 | 44.75 ± 2.84 | −20.75 |
|  | 2.50 | 62.00 ± 2.04 | 37.25 ± 1.11 | −24.75 |
| 9b | 0.25 | 72.50 ± 6.20 | 70.25 ± 8.39 | −2.25 |
|  | 1.00 | 73.25 ± 6.24 | 69.75 ± 7.44 | −3.50 |
|  | 2.50 | 72.50 ± 5.24 | 59.75 ± 4.82 | −12.75 |

TABLE IV

| substance + dose | time (min.) after admin. | frequency min$^{-1}$ | blood pressure mm. Hg | Δ | dp/dt mm sec | Δ |
|---|---|---|---|---|---|---|
| ISDN | 0 | 174.3 ± 9.3 | 104.3 ± 7.7 | −13.9 | 8800 ± 831 | −800 |
| 5 mg/kg | 10 | 179.3 ± 7.7 | 90.4 ± 12.5 | −13.1 | 8000 ± 1097 | −1133 |
|  | 30 | 177.7 ± 7.7 | 91.2 ± 10.0 | −10.1 | 7667 ± 807 | −1167 |
|  | 60 | 175.0 ± 8.6 | 94.2 ± 9.2 | −9.3 | 7633 ± 743 | −1750 |
|  | 120 | 167.7 ± 9.4 | 95.0 ± 9.6 |  | 7050 ± 661 |  |
| 1c/2c | 0 | 171.6 ± 6.2 | 124.2 ± 8.3 | −15.6 | 7220 ± 611 | +280 |
| 5 mg/kg | 10 | 180.4 ± 4.3 | 108.6 ± 8.5 | −16.4 | 7500 ± 522 | −260 |
|  | 30 | 177.2 ± 5.4 | 107.8 ± 8.4 | −17.6 | 6960 ± 564 | −120 |
|  | 60 | 177.6 ± 5.1 | 106.6 ± 7.8 | −18.0 | 7100 ± 721 | −220 |
|  | 120 | 178.8 ± 4.4 | 106.2 ± 5.6 |  | 7000 ± 1026 |  |

Legend:
Heart frequency, blood pressure and inotropism at different times after intraduodenal administration of ISDN or substance 1c/2c to cats.
Average values + standard errors from groups of 6 animals.

TABLE V (comparison): ISDN

|  | v | 2 | 5 | 7 | 10 | 15 | 20 | 25 |
|---|---|---|---|---|---|---|---|---|
| HF | 109.5 | 143.7 | 133.5 | 128.7 | 121.7 | 118.2 | 112.5 | 112.0 |
|  | ±7.1 | ±5.1 | ±11.9 | ±11.1 | ±10.6 | ±9.8 | ±8.8 | ±8.5 |
| $AP_{syst}$ | 166.9 | 145.7 | 152.9 | 152.9 | 152.9 | 154.8 | 154.8 | 156.6 |
|  | ±4.9 | ±7.9 | ±6.4 | ±6.5 | ±5.6 | ±4.7 | ±5.6 | ±4.7 |
| $AP_{diast}$ | 95.6 | 99.4 | 102.2 | 100.3 | 98.4 | 98.4 | 96.6 | 98.4 |
|  | ±10.8 | ±9.7 | ±7.7 | ±8.0 | ±9.0 | ±9.0 | ±7.4 | ±7.2 |
| PRA | 2.06 | 1.12 | 1.72 | 1.78 | 1.87 | 1.97 | 2.15 | 2.38 |
|  | ±0.5 | ±0.6 | ±0.7 | ±0.7 | ±0.6 | ±0.7 | ±0.7 | ±0.8 |
| $\overline{PAP}$ | 14.3 | 11.1 | 11.5 | 12.6 | 12.6 | 12.7 | 12.6 | 13.3 |
|  | ±1.2 | ±0.7 | ±0.8 | ±1.4 | ±1.4 | ±1.6 | ±1.3 | ±1.5 |
| LVEDP | 7.69 | 4.97 | 5.81 | 6.0 | 6.28 | 6.47 | 6.75 | 7.03 |
|  | ±1.3 | ±1.1 | ±0.8 | ±0.9 | ±0.8 | ±0.7 | ±0.7 | ±0.7 |
| dp/dt | 2268.7 | 2868.7 | 2606.2 | 2587.5 | 2550.0 | 2512.5 | 2418.7 | 2456.2 |
|  | ±271.1 | ±370.4 | ±30.1 | ±291.0 | ±302.2 | ±288.0 | ±281.0 | ±295.9 |
| $HL_L$ | 0.76 | 0.94 | 0.95 | 0.85 | 0.84 | 0.79 | 0.78 | 0.76 |
|  | ±0.13 | ±0.15 | ±0.17 | ±0.14 | ±0.15 | ±0.14 | ±0.13 | ±0.13 |
| $HL_R$ | 85.1 | 85.3 | 81.4 | 83.0 | 82.4 | 78.9 | 75.3 | 76.3 |
|  | ±19.8 | ±11.3 | ±13.9 | ±18.3 | ±17.9 | ±21.3 | ±16.3 | ±18.2 |
| SV | 27.7 | 26.3 | 27.4 | 25.9 | 27.4 | 26.8 | 27.9 | 26.8 |
|  | ±2.8 | ±1.8 | ±2.1 | ±1.5 | ±1.9 | ±2.3 | ±2.3 | ±2.1 |

TABLE V-continued (comparison): ISDN

| | | | | | | | |
|---|---|---|---|---|---|---|---|
| $BF_{Fem}$ | 44.9 | 31.2 | 35.4 | 37.3 | 38.4 | 40.9 | 40.9 | 41.9 |
| | ±11.7 | ±6.5 | ±7.7 | ±7.1 | ±6.6 | ±8.6 | ±7.2 | ±8.5 |
| $W_{Fem}$ | 0.39 | 0.55 | 0.49 | 0.45 | 0.42 | 0.41 | 0.40 | 0.40 |
| | ±0.1 | ±0.1 | ±0.1 | ±0.1 | ±0.05 | ±0.1 | ±0.05 | ±0.1 |
| HZV | 3.03 | 3.8 | 3.7 | 3.3 | 3.4 | 3.2 | 3.1 | 3.0 |
| | ±0.4 | ±0.4 | ±0.5 | ±0.4 | ±0.4 | ±0.4 | ±0.4 | ±0.4 |
| $W_{AP}$ | 0.31 | 0.23 | 0.22 | 0.27 | 0.26 | 0.26 | 0.25 | 0.27 |
| | ±0.05 | ±0.05 | ±0.04 | ±0.03 | ±0.03 | ±0.03 | ±0.02 | ±0.02 |
| $W_{TP}$ | 5.27 | 4.02 | 4.39 | 4.72 | 4.66 | 4.96 | 4.92 | 5.22 |
| | ±0.4 | ±0.1 | ±0.4 | ±0.3 | ±0.3 | ±0.3 | ±0.3 | ±0.4 |

| | 30 | 40 | 50 | 60 | 90 | 120 | 150 | 180 |
|---|---|---|---|---|---|---|---|---|
| HF | 110.0 | 108.0 | 109.2 | 107.5 | 109.5 | 104.2 | 103.7 | 103.7 |
| | ±17.5 | ±9.8 | ±21.2 | ±10.1 | ±9.9 | ±7.7 | ±6.9 | ±5.9 |
| $AP_{syst}$ | 155.6 | 158.4 | 157.5 | 159.4 | 163.2 | 161.2 | 161.2 | 161.2 |
| | ±3.2 | ±4.9 | ±5.1 | ±5.8 | ±5.8 | ±6.6 | ±4.7 | ±4.8 |
| $AP_{diast}$ | 98.1 | 101.2 | 101.2 | 101.2 | 99.4 | 97.5 | 95.6 | 95.6 |
| | ±5.9 | ±6.5 | ±6.5 | ±6.5 | ±5.6 | ±5.5 | ±4.5 | ±5.6 |
| PRA | 2.34 | 2.34 | 2.29 | 2.53 | 2.53 | 2.81 | 3.0 | 2.81 |
| | ±0.7 | ±0.7 | ±0.6 | ±0.7 | ±0.7 | ±0.8 | ±0.9 | ±0.8 |
| $\overline{PAP}$ | 13.5 | 14.0 | 14.0 | 14.1 | 14.6 | 15.0 | 14.6 | 15.5 |
| | ±1.5 | ±1.5 | ±1.6 | 1.6 | ±1.8 | ±2.0 | ±1.5 | ±1.6 |
| LVEDP | 7.22 | 7.60 | 7.60 | 7.77 | 7.98 | 8.34 | 7.78 | 7.60 |
| | ±0.6 | ±0.7 | ±0.7 | ±0.7 | ±0.9 | ±1.0 | ±1.0 | ±1.2 |
| dp/dt | 2390.6 | 2343.7 | 2306.2 | 2250.0 | 2231.2 | 2118.7 | 2025.0 | 2043.7 |
| | ±284.9 | ±281.2 | ±269.2 | ±250.6 | ±251.2 | ±221.5 | ±181.1 | ±206.2 |
| $HL_L$ | 0.76 | 0.76 | 0.77 | 0.78 | 0.77 | 0.72 | 0.74 | 0.79 |
| | ±0.10 | ±0.13 | ±0.13 | ±0.14 | ±0.12 | ±0.10 | ±0.10 | ±0.12 |
| $HL_R$ | 78.6 | 80.5 | 81.1 | 81.9 | 85.4 | 81.5 | 79.7 | 92.4 |
| | ±16.5 | ±17.2 | ±18.6 | ±20.1 | ±20.5 | ±18.9 | ±17.2 | ±18.7 |
| SV | 27.8 | 27.7 | 27.4 | 28.2 | 27.7 | 28.1 | 28.6 | 30.6 |
| | ±2.1 | ±1.9 | ±1.6 | ±1.6 | ±1.9 | ±1.8 | ±1.6 | ±1.9 |
| $BF_{Fem}$ | 41.5 | 42.9 | 43.9 | 42.3 | 44.4 | 49.3 | 51.3 | 53.7 |
| | ±8.1 | ±8.2 | ±9.2 | ±8.9 | ±8.2 | ±7.7 | ±9.8 | ±10.8 |
| $W_{Fem}$ | 0.40 | 0.40 | 0.39 | 0.41 | 0.38 | 0.33 | 0.32 | 0.32 |
| | ±0.1 | ±0.05 | ±0.1 | ±0.1 | ±0.04 | ±0.03 | ±0.05 | ±0.06 |
| HZV | 3.0 | 3.0 | 3.0 | 3.0 | 3.0 | 2.9 | 3.0 | 3.2 |
| | ±0.3 | ±0.3 | ±0.4 | ±0.4 | ±0.4 | ±0.2 | ±0.3 | ±0.3 |
| $W_{AP}$ | 0.27 | 0.28 | 0.27 | 0.26 | 0.27 | 0.28 | 0.29 | 0.31 |
| | ±0.03 | ±0.04 | ±0.04 | ±0.03 | ±0.06 | ±0.08 | ±0.05 | ±0.05 |
| $W_{TP}$ | 5.13 | 5.41 | 5.38 | 5.32 | 5.35 | 5.36 | 5.22 | 4.89 |
| | ±0.4 | ±0.5 | ±0.5 | ±0.5 | ±0.6 | ±0.3 | ±0.3 | ±0.3 |

TABLE VI

Compound acc. to Example 1c/2c

| | ν | 2 | 5 | 7 | 10 | 15 | 20 | 25 |
|---|---|---|---|---|---|---|---|---|
| HF | 97.5 | 158.7 | 148.7 | 146.7 | 141.2 | 133.0 | 129.7 | 125.7 |
| | ±13.0 | ±20.7 | ±22.1 | ±22.5 | ±22.5 | ±21.9 | ±19.6 | ±19.1 |
| $AP_{syst}$ | 150.9 | 115.3 | 120.9 | 121.9 | 120.9 | 120.4 | 121.5 | 122.8 |
| | ±8.4 | ±13.8 | ±13.3 | ±11.6 | ±10.6 | ±9.3 | ±8.7 | ±8.8 |
| $AP_{diast}$ | 88.1 | 74.1 | 82.5 | 83.4 | 83.4 | 80.6 | 79.1 | 80.6 |
| | ±7.7 | ±10.0 | ±9.4 | ±9.4 | ±8.4 | ±7.7 | ±6.7 | ±6.6 |
| PRA | 3.94 | 2.06 | 2.81 | 2.81 | 2.95 | 3.24 | 3.30 | 3.28 |
| | ±0.19 | ±0.45 | ±0.57 | ±0.45 | ±0.50 | ±0.54 | ±0.52 | ±0.41 |
| $\overline{PAP}$ | 15.8 | 15.6 | 13.7 | 14.1 | 14.2 | 14.0 | 13.8 | 14.0 |
| | ±1.4 | ±2.1 | ±1.4 | ±1.6 | ±1.6 | ±1.9 | ±1.7 | ±1.8 |
| LVEDP | 5.53 | 2.62 | 2.91 | 2.91 | 3.20 | 3.37 | 3.56 | 4.03 |
| | ±1.3 | ±0.6 | ±0.8 | ±0.8 | ±0.8 | ±0.8 | ±0.9 | ±1.0 |
| dp/dt | 2081.2 | 2606.2 | 2343.7 | 2362.5 | 2268.7 | 2250.0 | 2231.2 | 2175.0 |
| | ±253.2 | ±345.5 | ±251.3 | ±255.2 | ±309.8 | ±366.8 | ±330.3 | ±310.7 |
| $HL_L$ | 0.83 | 0.75 | 0.74 | 0.72 | 0.72 | 0.72 | 0.72 | 0.74 |
| | ±0.08 | ±0.13 | ±0.08 | ±0.06 | ±0.06 | ±0.06 | ±0.05 | ±0.05 |
| $HL_R$ | 96.0 | 115.8 | 87.6 | 89.3 | 88.8 | 87.3 | 87.7 | 90.0 |
| | ±15.4 | ±18.1 | ±5.1 | ±16.9 | ±17.6 | ±20.0 | ±20.0 | ±20.2 |
| SV | 38.3 | 25.6 | 26.0 | 25.6 | 26.4 | 29.3 | 30.0 | 31.3 |
| | ±3.6 | ±2.6 | ±4.0 | ±4.1 | ±3.7 | ±5.0 | ±4.4 | ±4.6 |
| $BF_{Fem}$ | 53.4 | 35.3 | 36.6 | 38.6 | 39.5 | 39.9 | 41.2 | 42.2 |
| | ±7.5 | ±4.0 | ±4.0 | ±4.2 | ±4.3 | ±5.2 | ±5.3 | ±5.4 |
| $W_{Fem}$ | 0.28 | 0.35 | 0.36 | 0.34 | 0.33 | 0.32 | 0.31 | 0.31 |
| | ±0.04 | ±0.08 | ±0.06 | ±0.06 | ±0.05 | ±0.05 | ±0.04 | ±0.05 |
| HZV | 3.61 | 3.91 | 3.61 | 3.51 | 3.50 | 3.61 | 3.66 | 3.70 |
| | ±0.25 | ±0.27 | ±0.08 | ±0.16 | ±0.11 | ±0.21 | ±0.18 | ±0.18 |
| $W_{AP}$ | 0.38 | 0.45 | 0.40 | 0.42 | 0.42 | 0.40 | 0.37 | 0.36 |

TABLE VI-continued

Compound acc. to Example 1c/2c

| | | | | | | | | |
|---|---|---|---|---|---|---|---|---|
| $W_{TP}$ | ±0.03<br>3.94<br>±0.3 | ±0.09<br>2.93<br>±0.3 | ±0.07<br>3.42<br>±0.4 | ±0.06<br>3.59<br>±0.5 | ±0.06<br>3.57<br>±0.4 | ±0.08<br>3.41<br>±0.4 | ±0.07<br>3.32<br>±0.4 | ±0.08<br>3.33<br>±0.4 |
| | 30 | 40 | 50 | 60 | 90 | 120 | 150 | 180 |
| HF | 122.7<br>±18.5 | 120.7<br>±17.4 | 118.7<br>±18.3 | 114.2<br>±20.1 | 107.5<br>±17.5 | 98.7<br>±11.7 | 97.5<br>±11.1 | 95.5<br>±8.5 |
| $AP_{syst}$ | 122.8<br>±8.8 | 126.6<br>±8.8 | 131.2<br>±8.9 | 133.1<br>±9.8 | 136.9<br>±10.9 | 143.4<br>±7.2 | 147.2<br>±7.1 | 143.4<br>±6.2 |
| $AP_{diast}$ | 79.7<br>±7.1 | 81.0<br>±6.8 | 83.4<br>±6.2 | 87.6<br>±6.2 | 87.6<br>±6.1 | 93.7<br>±3.4 | 94.7<br>±3.9 | 91.9<br>±3.9 |
| PRA | 3.52<br>±0.61 | 3.37<br>±0.59 | 3.43<br>±0.55 | 3.37<br>±0.59 | 3.85<br>±0.52 | 3.94<br>±0.49 | 4.03<br>±0.39 | 4.12<br>±0.31 |
| PAP | 14.1<br>±1.8 | 14.1<br>±1.8 | 13.9<br>±1.9 | 14.1<br>±2.0 | 14.5<br>±2.1 | 15.1<br>±2.3 | 15.1<br>±1.5 | 14.9<br>±1.3 |
| LVEDP | 4.31<br>±1.1 | 4.41<br>±1.2 | 4.69<br>±1.2 | 4.78<br>±1.3 | 5.25<br>±1.4 | 6.37<br>±1.2 | 6.97<br>±1.4 | 7.69<br>±1.3 |
| dp/dt | 2184.4<br>±330.6 | 2137.5<br>±327.6 | 2118.5<br>±315.8 | 2118.5<br>±335.9 | 2081.2<br>±380.4 | 2043.7<br>±402.0 | 1950.0<br>±373.7 | 1593.7<br>±297.4 |
| $HL_L$ | 0.73<br>±0.06 | 0.76<br>±0.05 | 0.75<br>±0.04 | 0.79<br>±0.05 | 0.82<br>±0.04 | 0.89<br>±0.06 | 0.91<br>±0.05 | 0.91<br>±0.06 |
| $HL_R$ | 84.9<br>±17.7 | 89.3<br>±19.6 | 83.6<br>±20.3 | 89.5<br>±21.8 | 91.5<br>±26.7 | 98.7<br>±29.7 | 98.0<br>±21.3 | 98.5<br>±20.0 |
| SV | 31.6<br>±4.5 | 32.7<br>±4.5 | 32.0<br>±4.7 | 35.6<br>±5.8 | 37.1<br>±4.4 | 40.0<br>±2.7 | 41.0<br>±3.3 | 42.6<br>±1.9 |
| $BF_{Fem}$ | 43.9<br>±4.9 | 46.3<br>±4.3 | 50.6<br>±4.5 | 50.4<br>±5.5 | 50.8<br>±6.6 | 58.6<br>±7.9 | 58.2<br>±8.1 | 59.4<br>±6.3 |
| $W_{Fem}$ | 0.29<br>±0.04 | 0.27<br>±0.03 | 0.26<br>±0.02 | 0.26<br>±0.03 | 0.27<br>±0.03 | 0.25<br>±0.03 | 0.26<br>±0.04 | 0.24<br>±0.02 |
| HZV | 3.63<br>±0.05 | 3.72<br>±0.10 | 3.55<br>±0.08 | 3.73<br>±0.03 | 3.77<br>±0.16 | 3.85<br>±0.23 | 3.89<br>±0.18 | 4.03<br>±0.23 |
| $W_{AP}$ | 0.36<br>±0.10 | 0.35<br>±0.10 | 0.34<br>±0.10 | 0.33<br>±0.10 | 0.32<br>±0.09 | 0.30<br>±0.07 | 0.27<br>±0.05 | 0.24<br>±0.03 |
| $W_{TP}$ | 3.32<br>±0.2 | 3.34<br>±0.3 | 3.61<br>±0.3 | 3.46<br>±0.2 | 3.59<br>±0.4 | 3.72<br>±0.3 | 3.73<br>±0.2 | 3.51<br>±0.3 |

For informing examination of acute toxicity of some of the compounds according to the invention, said compounds were intravenously administered in physiological saline solution to female NMRI-albino mice in doses of 50, 100 and 200 mg/kg, respectively. The compounds were injected to at least 3 animals per dose. If no animal had yet been died following to the highest dose which was administered, no more doses of substances were tested. In case of doubt, the examination was repeated with at least 3 more animals applying the same dose.

The rate of death within 24 hours after administration was observed.

In table VII, the determined rates of death as well as the LD$_{50}$-ranges evaluated therefrom are shown.

TABLE VII

| Compound according to example | Frequency of death with an intravenous dose of | | | Evaluated LD$_{50}$-range (mg/kg) |
|---|---|---|---|---|
| | 200 mg/kg | 100 mg/kg | 50 mg/kg | |
| 3 c | 3/3 | 0/6 | — | 100–200 |
| 4 b | 3/3 | 3/3 | 0/3 | 50–100 |
| 5 b | 3/3 | 3/6 | 1/11 | 50–100 |
| 6 b | 3/3 | 3/3 | 0/3 | 50–100 |
| 9 b | 3/3 | 4/6 | — | 50–100 |
| 2 c[+] | 0/6 | — | — | >200 |

[+] LD$_{70}$ p.o. mouse = 1600 mg/kg and LD$_{50}$ i.p. mouse = 540 mg/kg (534.7–545.4; according to Lichtfield and Wilcoxon).

We claim:
1. Adenyldesoxy-1.4;3.6-dianhydrohexitol nitrates having the formula Ia

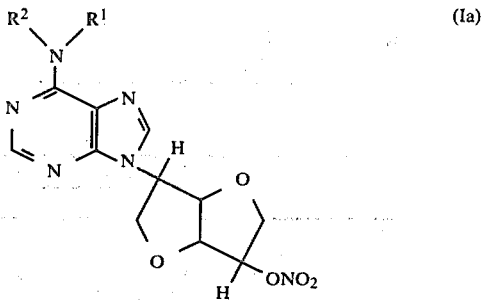

wherein $R^1$ and $R^2$ are the same or different and, independently of one another signify
(a) a hydrogen atom,
(b) a straight-chained or branched alkyl group with 1 to 7 C-atoms,
(c) an ω-phenylalkyl group, whereby the alkyl group has 1 to 7 C-atoms and whereby the phenyl ring can be halogen-substituted in the p-position, or wherein
(d) $R^1$ signifies one of the residues given under (a) to (c) and $R^2$ an acyl radical of an aliphatic non-cyclic saturated monocarboxylic acid with 2 to 7 C-atoms, or wherein
(e) $R^1$ and $R^2$, together with the nitrogen atom to which they are bound, represent the residue of a cyclic, non-aromatic, secondary amine selected from the group consisting of pyrrolidine, piperidine, piperazine, morpholine, and 4-methyl-piperazine, as well as their physiologically acceptable acid-addition salts.

2. 5-(9-Adenyl)-5-desoxy-1.4;3.6-dianhydro-L-iditol 2-nitrates of the general formula Ic

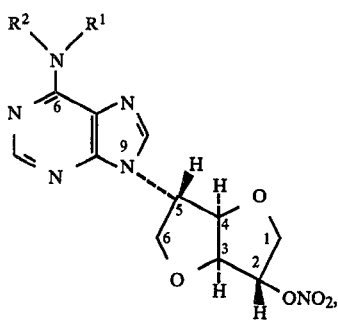

wherein $R^1$ and $R^2$ possess the meanings mentioned in claim 1, as well as their physiologically acceptable acid-addition salts.

3. 2-(9-Adenyl)-2-desoxy-1.4;3.6-dianhydro-D-glucitol 5-nitrates of the general formula Id

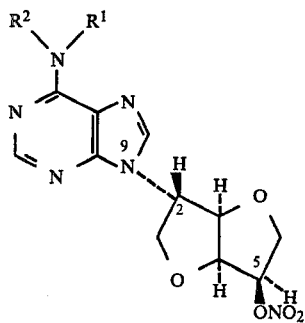

wherein $R^1$ and $R^2$ possess the meanings mentioned in claim 1, as well as their physiologically acceptable acid-addition salts.

4. 5-(9-Adenyl)-5-desoxy-1.4;3.6-dianhydro-D-glucitol 2-nitrates of the general formula Ie

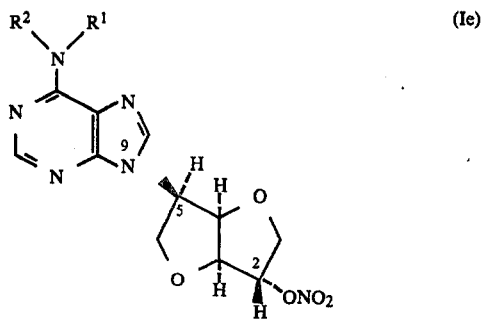

wherein $R^1$ and $R^2$ possess the meanings mentioned in claim 1, as well as their physiologically acceptable acid-addition salts.

5. The nitrates of claim 1 wherein $R^2$ is an acyl radical of a methyl substituted monocarboxylic acid.

6. The nitrates of claim 1 wherein the cyclic, non-aromatic secondary amine contains an additional hetero atom.

7. 5-(9-Adenyl)-5-desoxy-1.4;3.6-dianhydro-L-iditol 2-nitrate.

8. 5-(6-Methylaminopurin-9-yl)-5-desoxy-1.4;3.6-dianhydro-L-iditol 2-nitrate.

9. 5-(6-Dimethylaminopurin-9-yl)-5-desoxy-1.4;3.6-dianhydro-L-iditol 2-nitrate.

10. 5-(6-Ethylaminopurin-9-yl)-5-desoxy-1.4;3.6-dianhydro-L-iditol 2-nitrate.

11. 5-(6-Pyrrolidinopurin-9-yl)-5-desoxy-1.4;3.6-dianhydro-L-iditol 2-nitrate.

12. 5-(6-Piperidinopurin-9-yl)-5-desoxyl-1.4;3.6-dianhydro-L-iditol 2-nitrate.

13. 5-(6-Morpholinopurin-9yl)-5-desoxy-1.4;3.6-dianhydro-L-iditol 2-nitrate.

14. 5-[6-(4-Methylpiperazino)-purin-9-yl]-5-desoxy-1.4;3.6-dianhydro-L-iditol 2-nitrate.

15. 5-[9-(6-N-Pivaoyl)-adenyl]5-desoxy-1.4;3.6-dianhydro-L-iditol 2-nitrate.

16. 5-[9-(6-N-Acetyl)-adenyl]-5-desoxy-1.4;3.6-dianhydro-L-iditol 2-nitrate.

17. 5-(6-Benzylaminopurin-9-yl)-5-desoxy-1.4;3.6-dianhydro-L-iditol 2-nitrate.

18. 5-[6-(3-Phenylpropyl)-aminopurin-9-yl]-5-desoxy-1.4;3.6-dianhydro-L-iditol 2-nitrate.

19. 2(9-Adenyl)-2-desoxy-1.4;3.6-dianhydro-D-glucitol 5-nitrate.

20. 5-{6-[3-(4-Chlorophenyl)-propylamino]-purin-9-yl}-5desoxy-1.4;3.6-dianhydro-L-iditol 2-nitrate.

21. A composition for treating coronary diseases comprising a pharmaceutically effective amount of the nitrate of claim 1 and pharmaceutically acceptable carriers therefor.

22. A method for the treatment of coronary disease in humans comprising administering a pharmaceutically effective amount of the composition of claim 21.

* * * * *